United States Patent
Silverman et al.

(10) Patent No.: US 9,212,359 B2
(45) Date of Patent: Dec. 15, 2015

(54) SYSTEMS FOR INDUCTION OF GENE EXPRESSION AND PROTEIN DEPLETION IN YEAST

(76) Inventors: Sanford Jay Silverman, Roosevelt, NJ (US); Robert Scott McIsaac, Princeton, NJ (US); Marcus Noyes, Monmouth Junction, NJ (US); David Botstein, Princeton, NJ (US)

( * ) Notice: Subject to any disclaimer, the term of this patent is extended or adjusted under 35 U.S.C. 154(b) by 0 days.

(21) Appl. No.: 14/128,700

(22) PCT Filed: Jun. 15, 2012

(86) PCT No.: PCT/US2012/042617
§ 371 (c)(1),
(2), (4) Date: Dec. 23, 2013

(87) PCT Pub. No.: WO2012/177499
PCT Pub. Date: Dec. 27, 2012

(65) Prior Publication Data
US 2014/0128287 A1 May 8, 2014

Related U.S. Application Data

(60) Provisional application No. 61/618,248, filed on Mar. 30, 2012, provisional application No. 61/608,788, filed on Mar. 9, 2012, provisional application No. 61/500,367, filed on Jun. 23, 2011.

(51) Int. Cl.
*C12N 15/79* (2006.01)
*C12N 15/10* (2006.01)
*C12N 15/63* (2006.01)
*C12N 15/81* (2006.01)

(52) U.S. Cl.
CPC ............ *C12N 15/1079* (2013.01); *C12N 15/63* (2013.01); *C12N 15/81* (2013.01)

(58) Field of Classification Search
CPC ............ C37K 2319/81; C37K 2319/95; C12N 15/79; C12N 15/10; C12N 15/1079; C12Q 1/37
See application file for complete search history.

(56) References Cited

U.S. PATENT DOCUMENTS

| 5,093,242 A | 3/1992 | Bachmair et al. |
| 5,122,463 A | 6/1992 | Varshavsky et al. |
| 5,132,213 A | 7/1992 | Bachmair et al. |
| 5,196,321 A | 3/1993 | Bachmair et al. |

OTHER PUBLICATIONS

Taxis et al. Efficient protein depletion by genetically controlled deprotection of a dormant N-degron. Mol. Syst. Biol. 2009, vol. 5, Article No. 267, pp. 1-7.
Quintero et al. An improved system for estradiol-dept. regulation of gene expression in yeast. Microb. Cell Fact Mar. 20, 2007, vol. 6, No. 10, pp. 1-9.
Sera et al. Rational Design of Artificial Zinc-Finger Proteins Using a Nondegenerate Recognition Code Table. American Chem. Society 2002, vol. 41, pp. 7074-7081.
Louvion et al. Fusion of GAL4-VP16 to a steroid-binding domain provides a tool for a gratuitous induction of galactose-responsive genes in yeast. Gene. 1993, vol. 131, pp. 129-134.
Hickman et al. Coordinated regulation of sulfur and phospholipid metabolism reflects the importance of methylation in the growth of yeast. Mol. Bio. of the Cell Nov. 1, 2011, vol. 22, pp. 4192-4204.
Veatch et al. Mitochondrial Dysfunction Leads to Nuclear Genome Instability via an Iron-Sulfur Cluster Defect. Cell Jun. 26, 2009, vol. 137, pp. 1247-1258.
Xu et al. A Versatile Framework for the Design of Ligand-Dependent, Transgene-Specific Transcription Factors. Molecular Therapy Feb. 2001, vol. 3, No. 2, pp. 262-273.
Boyle et al. Go:TermFinder—open source software for accessing Gene Ontology information and finding significantly enriched Gene Ontology terms associated with a list of genes. Bioformatics 2004, vol. 20, No. 18, pp. 3710-3715.
Brauer et al. Coordination of Growth Rate, Cell Cycle, Stress Response, and Metabolic Activity in Yeast. The American Society for Cell Biology Jan. 2008, vol. 19, pp. 352-367.
Cai et al. Frequency-modulated nuclear localization bursts coordinated gene regulation. Nature Sep. 25, 2008, vol. 455, pp. 485-491.
De Virgilio et al. Disruption of TPS2, the gene encoding the 100-kDa subunit of the trehalose-6-phosphate synthase/phosphatase complex in *Saccharomyces cerevisiae*, causes accumulation of trehalose-6-phosphate and loss of trehalose-6-phosphate phosphatase activity. European Journal of Biochemistry 1993, vol. 212, pp. 315-323.
Gaisne et al. A 'natural' mutation in *Saccharomyces cerevisiae* strains derived from S288c affects the complex regulatory gene HAP1 (CYP1). Current Genetics 1999, vol. 36, pp. 195-200.
Gao et al. Tightly Regulated, Beta-Estradiol Dose-Dependent Expression System for Yeast. Bio Techniques Dec. 2000, vol. 29, pp. 1226-1231.
Gill et al. Negative effect of the transcriptional activator GAL4. Nature Aug. 25, 1988, vol. 334, pp. 721-724.
Giniger et al. Specific DNA Binding of GAL4, A Positive Regulatory Protein of Yeast. Cell Apr. 1985, vol. 40, pp. 767-774.
Goldstein et al. Three New Dominant Drug Resistance Cassettes for Gene Disruption in *Saccharomyces cerevisiae*. Yeast Functional Analysis Reports 1999, vol. 15, pp. 1541-1553.

(Continued)

*Primary Examiner* — Karen Cochrane Carlson

(57) ABSTRACT

A system allows for rapid and specific induction of individual genes in eukaryotic cells using a chimeric transcriptional activator that is responsive to hormone inducer. Upon addition of the hormone, cytoplasmic transcriptional activator localizes to the nucleus and subsequently binds to promoters containing sequences that bind to its DNA-binding domain. Genetic modifications allow for rapid and specific degradation of a targeted protein upon addition of hormone by means of a regulated degron method that utilizes a protease variant. This system is useful for discovering new compounds by high throughput screening when introducing compound libraries to these protein-depleted cells.

8 Claims, 22 Drawing Sheets

(56) References Cited

OTHER PUBLICATIONS

Guarente et al. Fusion of *Escherichia coli* lacZ to the cytochrome c gene of *Saccharomyces cerevisiae*. Proc. Natl. Acad. Sci. USA Apr. 1981, vol. 78, No. 4, pp. 2199-2203.
Guldener et al. A second set of loxP marker cassettes for Cre-mediated multiple gene knockouts in budding yeast. Nucleic Acids Research 2002, vol. 30 No. 6, pp. 1-8.
Hersen et al. Signal processing by the HOG MAP kinase pathway. PANS May 20, 2008, vol. 105, No. 20, pp. 7165-7170.
Hickman et al. Heme Levels Switch the Function of Hap1 of *Saccharomyces cerevisiae* between Transcriptional Activator and Transcriptional Repressor. Molecular and Cellular Biology Nov. 2007, vol. 27, No. 21, pp. 7414-7424.
Hong et al. Structural Basis for Dimerization in DNA Recognition by Gal. Structure Jul. 2008, vol. 16, pp. 1019-1026.
Hovland et al. Galactose as a gratuitous inducer of GAL gene expression in yeasts growing on glucose. Gene 1989, vol. 83, pp. 57-64.
Kahm et al. grot: Fitting Biological Growth Curves with R. Journal of Statistics Software Feb. 2010, vol. 33, No. 7, pp. 2-21.
Labow et al. Conversion of the lac Repressor into an Allosterically Regulated Transcriptional Activator for Mammalian Cells. Molecular and Cellular Biology Jul. 1990, vol. 10, No. 7, pp. 3343-3356.
Liko et al. Using the yeast gene deletion collection to customize gene expression. Bio. Techniques Jun. 2006, vol. 40, No. 6, pp. 728-734.
Liu et al. Nucleic Acids, Protein Synthesis, and Molecular Genetics: The Yeast Hsp110 Family Member, Sse1, Is an Hsp90 Cochaperone. The Journal of Biological Chemistry 1999, vol. 274, No. 38, pp. 26654-26660.
Longtine et al. Additional Modules for Versatile and Economical PCR-based Gene Deletion and Modification in *Saccharomyces cerevisiae*. Yeast 1998, vol. 14, pp. 953-961.
Lu et al. Slow Growth Induces Heat-Shock Resistance in Normal and Respiratory-deficient Yeast. Molecular Biology of the Cell Feb. 1, 2009, vol. 20, pp. 891-903.
Ma et al. Plasmid construction by homologous recombination in yeast. Gene 1987, vol. 58, pp. 201-216.
Marmorstein et al. DNA recognition by GAL4: structure of a protein—DNA complex. Nature Apr. 2, 1992, vol. 356, pp. 408-414.
Mason et al. Distinction and Relationship between Elongation Rate and Processivity of RNA Polymerase II In Vivo. Molecular Cell Mar. 18, 2005, vol. 17, 831-840.
Masselot et al. Methionine Biosynthesis in *Saccharomyces cerevisiae*. Molec. gen. Genet. 1975, vol. 139, pp. 121-132.
McClean et al. Measuring In Vivo Signaling Kinetics in a Mitogen-Activated Kinase Pathway Using Dynamic Input Stimulation. Methods in Molecular Biology 2011, vol. 734, pp. 101-119.
Pratt et al. Steroid Receptor Interactions with Heat Shock Protein and Immunophilin Chaperones. Endocrine Reviews 1997, vol. 18, No. 3, pp. 306-360.
Ronen et al. Transcriptional response of steady-state yeast cultures to transient perturbations in carbon source. PNAS Jan. 10, 2006, vol. 103, No. 2, pp. 389-394.
Rouillon et al. Feedback-regulated degradation of the transcriptional activator Met4 is triggered by the SCFMet30 complex. The EMBO Journal 2000, vol. 19, No. 2, pp. 282-294.
Sadowski et al. GAL4-VP16 is an unusually potent transcriptional activator. Nature Oct. 6, 1988, vol. 335, pp. 563-564.
Sheff et al. Optimized cassettes for fluorescent protein tagging in *Saccharomyces cerevisiae*. Yeast Functional Analysis Report 2004, vol. 21, pp. 661-670.
Sikorski et al. A System of Shuttle Vectors and Yeast Host Strains Designed for Efficient Manipulation of DNA in *Saccharomyces ceratisiae*. The Genetics Society of America May 1989, vol. 122, pp. 19-27.
Silverman et al. Metabolic cycling in single yeast cells from unsynchronized steady-state populations limited on glucose or phosphate. PNAS Apr. 13, 2010, vol. 107, No. 15, pp. 6946-6951.
Sternberg et al. Biomedical Image Processing. Computer Jan. 1983, vol. 16, No. 1, pp. 22-34.
Takahashi et al. Membrane Localization of Scaffold Proteins Promotes Graded Signaling in the Yeast MAP Kinase Cascade. Current Biology Aug. 26, 2008, vol. 18, No. 16, pp. 1184-1191.
Zenklusen et al. Single-RNA counting reveals alternative modes of gene expression in yeast. Nature Structural & Molecular Biology Dec. 2008, vol. 15, No. 12, pp. 1263-1271.
Guldener et al. A new efficient gene disruption cassette for repeated use in budding yeast. Nucleic Acids Research 1996, vol. 24, No. 13, pp. 2519-2524.
Pan and Coleman, "GAL4 Transcription Factor is Not a 'Zinc Finger' But Forms a Zn(II)2Cys6 Binuclear Cluster," (1990) Proc. Natl. Acad. Sci. USA, vol. 87, pp. 2077-2081.
Kim, J., & Pabp, C. "Getting a Handhold on DNA: Design of the Poly-Zinc Finger Proteins with Femtomolar Dissociation Constants", Proceedings of the National Academy of Sciences, Mar. 1998, vol. 95, pp. 2812-2817.
Noyes, M., "Analysis of Specific Protein-DNA Interactions by Bacterial One-Hybrid Assay", Methods in Molecular Biology (2012), vol. 786, pp. 79-95.

```
        M   S   I   T           S   L   Y           K   K   A       G   S   E   N       L   Y   F
  1   ATGTCTATTA  TACAGATAAT  CTTCTTTGTA  GAAGAAACAT  CAAGAAGGCT  GGTTCTGAAA  ACTTGTACTT
        Q   F   H                       K   S   G   A   W   K   L       P   V   S       L   V   K   R
 51   CCAATTCAC   GGTTAAGGTG  AAGTCGGTG   CTTGGAAGT   CCAAGACTTT  TGAACATGAA
        G   I   D                       K   L   D           Y   K   E       Q   L   Q   A       W   R   W
101   GAGGGATCGA  CTCCCTAGCT  TTCAGACCAC  GAACCTTGAT  GAACCTTGAA  GCCAGTTCT   TGGTTAAGA
        E   R   I                       D   E   R                   N   R   P               E   L   D
151   GAAAGAGAAA  CTTCCTTT    TAAGCTTGAT  TATAAAGAAC  AGCTTCAGGC  AACCAATTCT

A   M   F                       P   E   G   Y       K   V   L                           A   G   Y   V
201   TGCTATGTTC  ACGATACAAG  CCAGAAGGAT  AAATGCCCA   CTTCTCCTCA  AGGAATTAGA
        P   I   R                       T   P   A               H   M   D                       N   V   C
251   TTCCTATTCG  AAGGATAAGC  GGTCTTCTA   ATTCCATGA   TATTCCATGA  AGGAGGAGGT  GACCAATTAC
        Y   T   K   L       L   S   M
301   TATACGAAGT  TTGAGGTCGA  TATTATCGAT  CATATGGATA  TAACTTCGTA  TAATGTATGC
      ATATGCTTCA              ATAATAGCTA  GTATACCTAT  ATTGAAGCAT  ATTACATACG
                                          G
                                          C
```

*FIGURE 14*

SYSTEMS FOR INDUCTION OF GENE EXPRESSION AND PROTEIN DEPLETION IN YEAST

CROSS-REFERENCE TO RELATED APPLICATIONS

This application claims benefit of U.S. Provisional Applications No. 61/500,367, filed Jun. 23, 2011, No. 61/608,788, filed Mar. 9, 2012, and No. 61/618,248, filed Mar. 30, 2012, which are hereby incorporated in their entirety by reference.

STATEMENT OF GOVERNMENT INTEREST

This invention was made with government support under Grant GM046406 and Grant GM071508 awarded by the National Institutes of Health. The government has certain rights in this invention.

SEQUENCE LISTING

The instant application contains a Sequence Listing which has been submitted in ASCII format via EFS-Web and is hereby incorporated by reference in its entirety. Said ASCII copy, created on Jun. 13, 2012, is named PR-20776.txt and is 19,939 bytes in size.

FIELD OF THE INVENTION

The invention relates to the control of protein abundance in eukaryotes. More specifically, the invention relates to induction of targeted protein and to proteasomal degradation of specific protein.

BACKGROUND

Previous studies of the dynamics and functional relationships of genes and the networks they comprise followed gene expression after a well-defined perturbation to a culture growing in steady state. Traditionally, such perturbations involved a pulse of preferential carbon source, heat or nutrients (RONEN and BOTSTEIN 2006). However, when one wants to perturb only a single element of the system, such as a transcription factor, use of the traditional perturbation methods result in side effects on physiology and gene expression that can be deleterious to the experiment. What is needed to resolve this problem is finding specific ways of turning on (or off) only a single transcription factor.

Significant effort in the prior art had been placed on achieving tightly controlled gene expression systems across a spectrum of organisms, guided by the transformative discoveries of gratuitous inducers of expression of the lactose operon genes in E. coli. The significant desirable features of a useful induction system include (1) a complete lack of target gene activation in the absence of inducer, (2) rapid induction of a target gene in the presence of inducer, and (3) the availability of a truly gratuitous inducer. A gratuitous inducer should interact with no other regulatory system and should be essentially inert with respect to physiology.

A common approach in mammalian cells is a direct adaptation of bacterial systems: tetracycline-inducible tetR-based systems (LABOW et al. 1990). By fusing activating domains (e.g., VP16) to tetR and expressing this chimeric transcription factor, transcription of a target gene downstream of a minimally active promoter with the appropriate operator sites can be maintained at high levels in the absence of inducer. TetR-VP16, also called tTA (tetracycline transactivator), unbinds DNA in the presence of tetracycline, thereby repressing transcription. This configuration is referred to as tet-off. Tet-off has been used for studying the effects of depletion of a target gene, but the kinetics of transcriptional shut off do not result in rapid elimination of the protein products of the regulated genes, as many proteins have long half-lives. Therefore, a better method for rapid depletion of a target gene is needed.

The most widely used overexpression system in S. cerevisiae has utilized GAL4-mediated induction of targets, which are placed downstream of promoters containing 17-mer UASgal sites (such as $P_{GAL1}$, $P_{GAL7}$, $P_{GAL10}$), CGG-$N_{11}$-CCG (SEQ ID NO: 1) (GINIGER et al. 1985). The UASgal motif is recognized by dimerized GAL4 proteins (HONG et al. 2008; MARMORSTEIN et al. 1992). Deletion of GAL1 has made galactose overexpression of GAL-driven targets nearly gratuitous (HOVLAND et al. 1989). Since GAL genes are catabolite repressed, activation required that cells be grown in relatively poor, non-glucose carbon sources prior to the galactose pulse.

A more convenient system was developed that avoids the necessity of switching the carbon source. A chimeric transcriptional activator called GEV (LOUVION et al. 1993) contains the DNA binding domain of Gal4p, the hormone binding domain (HBD) of the human estrogen receptor (hER), and the highly electronegative portion of herpes simplex virus protein VP16, which confers strong transcriptional activity (SADOWSKI et al. 1988). Though GEV binds DNA via a GAL4 DNA binding domain, it is not subject to inhibition or repression by glucose, making it feasible to conduct induction and overexpression experiments in standard glucose-containing media simply by the addition of the inducer β-estradiol. The presence of the HBD provides a simple on/off switch for GEV activity; steroid receptor binding of ligand results in a conformational change of the receptor and its subsequent disassociation from the Hsp90 chaperone complex (PRATT and TOFT 1997).

Previously, improvements over the original GEV system were made by placing GEV expression under the control of low-strength constitutive promoters to reduce errant expression of target genes in the absence of β-estradiol (GAO and PINKHAM 2000; VEATCH et al. 2009). Another GEV-based induction system implemented an autocatalytic approach to rapidly increase GEV production in the presence of β-estradiol. In this case, GEV was placed under the control of the GAL1 promoter, which contains 4 UASgal sites (QUINTERO et al. 2007). However, the prior art only envisioned GEV for induction of gene expression.

SUMMARY OF THE INVENTION

Genetically modified yeast cells were created by a novel method involving transformation with a DNA construct to modify any target gene so that when expressed, a degradation signal (a dormant N-degron) is placed at the amino-terminus of the protein. Following transformation, the selectable drug marker used for the transformation was eliminated. The recipient cells were also modified to contain a hormone-responsive transcription factor and a protease-encoding gene induced by this transcription factor. Introduction of hormone into the cell medium results in activation of the transcription factor with minimal effects on the physiology and transcriptome of the cells except for target-specific degradation and downstream effects. The protease cleaves the dormant N-degron to initiate N-end rule degradation of the target protein.

The novel cell system allows rapid, specific target protein degradation in glucose grown cells of yeast such as S. cerevisiae. Additionally, the transcription factor, GEV, also rapidly induces single genes in a hybrid diploid yeast (e.g., S. cerevi-

*siae/S. bayanus*). The N-degron/GEV method extends to yeast, generally and, more generally extends to eukaryotes.

One aspect of the invention is a method of targeted protein depletion in a eukaryotic cell. The eukaryotic cell comprises (a) a target gene having a modified degron sequence at the initiator codon of the open reading frame, the target gene being capable of expressing a target protein; (b) a protease-encoding gene that expresses a protease that is capable of hydrolyzing the target protein to yield a protein having an N-end rule destabilizing amino acid at the amino terminus; and (c) a transcriptional activator comprising a DNA-binding domain and a hormone-binding domain, wherein, when bound by a hormone, the transcriptional activator induces expression of the protease-encoding gene. The method comprises exposing the eukaryotic cell to a hormone by contacting the cell with an effective amount of a hormone that binds to the hormone binding domain of the transcriptional activator, inducing expression of the protease by the protease-encoding gene. The protease cleaves the target protein to expose the N-end rule destabilizing amino acid and the target protein is degraded.

In one embodiment of this method, the DNA-binding domain is a GAL4 DNA binding domain, a zinc finger domain, or a DNA-binding domain of a transcriptional activator that is not from yeast.

In another embodiment of the method the hormone-binding domain is from the human estradiol receptor, the human glucocorticoid receptor or the human mineralocorticoid receptor.

In yet another embodiment of the method the transcriptional activator is GEV, the hormone is β-estradiol, and the protease-encoding gene encodes the tobacco etch virus (TEV) protease.

In still another embodiment of the method the protease-encoding gene is driven by a synthetic promoter operably linked to a modified TEV protease-coding region, a spliceosome subunit p14-peptide coding region, a terminator, and a selectable marker.

In another embodiment of the method the protease is TEV, HRV 2A or HRV 3C.

A related aspect of the invention is a eukaryotic cell comprising: (a) a target gene having a modified degron sequence at the initiator codon of the open reading frame, the target gene being capable of expressing a target protein, (b) a protease-encoding gene that expresses a protease capable of hydrolyzing the target protein to yield a cleaved target protein having an N-end rule destabilizing amino acid at the amino terminus, and (c) a transcriptional activator comprising a hormone-binding domain, wherein when bound by the hormone, the transcriptional activator induces expression of the protease-encoding gene.

In one embodiment, the cell's transcriptional activator is GEV, ZEV or 4ZEV, and the hormone is β-estradiol.

In yet another embodiment, the invention comprises modifying the chimeric transcriptional activator so that another DNA binding domain substitutes for the GAL4 DNA binding domain. Additionally or alternatively the transcriptional activator can be modified to replace the hER2 receptor binding domain with that of another receptor so that instead of requiring β-estradiol, an alternative ligand would bind and serve to activate the transcription factor.

Another related aspect of the invention is a transcriptional activator that is functional in a eukaryotic cell. The activator comprises a DNA-binding domain, an activation domain, and a hormone-binding domain wherein, when bound by a hormone the transcriptional activator induces transcription. The DNA-binding domain of the transcriptional activator is from a non-yeast transcription factor or from a customized zinc finger domain that recognizes DNA sequences not found in yeast. The hormone-binding domain is from the hormone-binding domain of a eukaryotic steroid hormone receptor. The activation domain is from a polypeptide sequence that comprises an acidic region. In one embodiment, the transcriptional activator is ZEV or 4ZEV.

A further aspect of the invention is a method of targeted protein induction in a eukaryotic cell. The cell comprises (a) a gene encoding a chimeric transcriptional activator operably linked to a constitutive promoter and (b) a target gene that expresses a target protein. The transcriptional activator comprises a hormone-binding domain, an activation domain, and a DNA-binding domain. The DNA-binding domain is from a transcription factor other than yeast or comprises a zinc finger domain that is engineered or rationally designed. The target gene is operably linked to a promoter that comprises a DNA sequence recognized by the DNA binding domain of the transcriptional activator. According to the method, the cell is exposed to an effective amount of a hormone that binds to the hormone binding domain. The-hormone-bound transcriptional activator induces the target gene to express the target protein.

A related aspect of the invention is a eukaryotic cell comprising: a gene encoding a chimeric transcriptional activator and a target gene that expresses a target protein. The gene encoding the transcriptional activator is operably linked to a constitutive promoter. The transcriptional activator comprises a hormone-binding domain, an activation domain, and a DNA-binding domain, wherein the DNA binding domain is from a transcription factor other than yeast or comprises a zinc finger domain that is engineered or rationally designed. The target gene is operably linked to a promoter that comprises a DNA sequence recognized by the DNA binding domain of the transcriptional activator.

In yet another related aspect, the invention features a method of constructing a targeted protein depletion system in a yeast cell transformed with a plasmid or chromosomally-integrating form of bacteriophage lambda CRE recombinase expressed by an inducible promoter. The method comprises (a) constructing a protease cassette comprising a yeast native promoter operably linked to a modified protease-coding region, a spliceosome subunit p14 peptide coding region, a CYC1 terminator, and a first selectable marker; (b) integrating the protease cassette into a chromosome of the yeast cell; (c) constructing a modified degron/marker cassette comprising modified degron-coding sequence and a second selectable marker, the marker being surrounded by a removable (loxP or other CRE recombinase removable) segment; (d) integrating the modified degron/marker cassette at the initiator methionine codon of the ORF of a gene coding for a target protein; and (e) inducing the CRE recombinase with an inducer, wherein the second selectable marker is removed.

A further related aspect of the invention features a method for high throughput screening for compounds that are candidates to structurally disrupt or metabolically inhibit a target protein having the capability to suppress growth of a eukaryotic cell. The method uses eukaryotic host cells comprising (a) a gene encoding a transcriptional activator operably linked to a constitutive promoter and (b) a target gene. The transcriptional activator comprises a hormone-binding domain, an activation domain, and a DNA-binding domain, wherein the DNA binding domain is from a transcription factor other than yeast or comprises a zinc finger domain that is engineered or rationally designed. The target gene is operably linked to a promoter that comprises a DNA sequence recognized by the DNA binding domain of the transcriptional activator. The target gene is capable of expressing a target protein that is an enzyme or structural protein that suppresses cell growth at high concentration. The method comprises: (a) contacting the cells with the hormone in an amount that provides a constant level of the target protein that results in a growth deficiency of the host cells; (b) exposing the host cells to a library of the candidate compounds; and (c) determining which compounds afford a growth advantage to the host cells. The compounds that afford the growth advantage are the candidates to inhibit or disrupt the target protein.

BRIEF DESCRIPTION OF THE DRAWINGS

FIG. 14: Amino acid (SEQ ID NO: 53) and DNA (SEQ ID NO: 52) sequence resulting from Cre-mediated loxP excision of the Kan/TDeg'F cassette inserted at any gene. The last ATG is the first ATG of the wild type gene.

DETAILED DESCRIPTION OF THE INVENTION

Definitions

Figure 1:
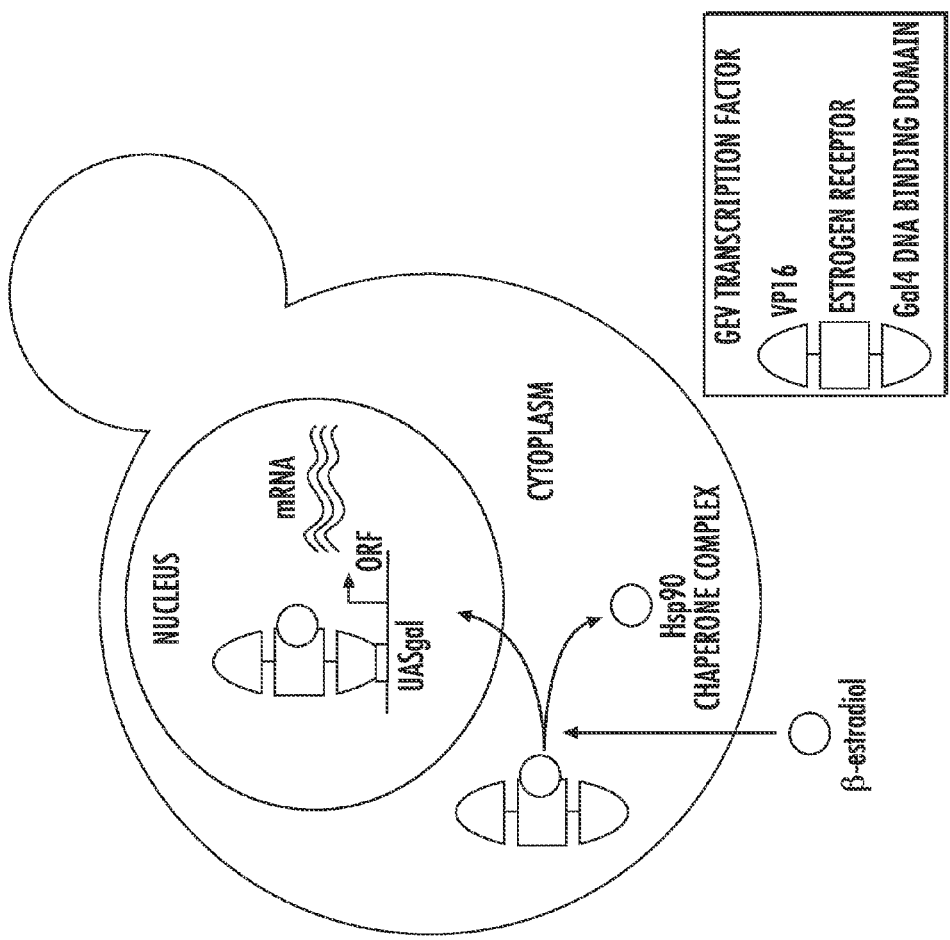
FIG. 1: Schematic of the GEV overexpression system. GEV is constitutively expressed from an ACT1 promoter. Prior to activation by β-estradiol, GEV is inactive in the cytoplasm, associating with the Hsp90 chaperone complex. β-estradiol diffuses through the cell membrane and binds to the GEV estrogen receptor domain, resulting in release of GEV from the Hsp90 chaperone complex. GEV then localizes to the nucleus, binding to UASgal consensus sequences, and strongly activates transcription via its VP16 domain.

The terms "peptide," "polypeptide," and "protein" are used interchangeably herein, and refer to a polymeric form of amino acids of any length.

By "construct" is meant a recombinant nucleic acid, generally recombinant DNA, which has been generated for the purpose of the expression of a specific nucleotide sequence(s), or is to be used in the construction of other recombinant nucleotide sequences.

"Operably linked" refers to a juxtaposition wherein the components so described are in a relationship permitting them to function in their intended manner. For instance, a promoter is operably linked to a coding sequence if the promoter affects its transcription or expression.

The term "transformation" refers to a permanent or transient genetic change induced in a cell following introduction of new nucleic acid (i.e., DNA exogenous to the cell). In a eukaryotic cell, a permanent genetic change is generally achieved by introduction of the DNA into the genome of the cell.

The N-degron is an intracellular degradation signal whose essential determinant is a specific ("destabilizing") N-terminal amino acid residue of a substrate protein. A set of N-degrons containing different destabilizing residues is manifested as the N-end rule, which relates the in vivo half-life of a protein to the identity of its N-terminal residue. The fundamental principles of the N-end rule, and the proteolytic pathway that implements it, are well established in the literature (see, e.g., Bachmair et al., Science 234: 179 (1986); Varshaysky. Cell 69: 725 (1992), U.S. Pat. Nos. 5,122,463; 5,132,213; 5,093,242 and 5,196,321) the disclosures of which are incorporated herein by reference in their entirety. A dormant N-degron is one that must be cleaved or degraded in order that the destabilizing residue becomes the N-terminal amino acid residue.

As used herein, TDeg'F is used synonomously with NDeg.

An estradiol-responsive transcription factor is one that has a hormone binding domain that binds to estradiol to activate the transcription factor.

The term "degrade" and "degradation" as used herein refer to proteolytic degradation as may be facilitated by a component of the N-end rule proteolytic pathway. Such a degradation is meant to describe the targeted degradation of a specific "target gene polypeptide."

The description of induction and degradation systems herein make reference to a modified target gene driven by its native promoter. Genes included in expression vectors must be driven by a nucleotide sequence comprising a regulatory element, for example, a promoter. Several types of promoters are well known in the transformation arts, as are other regulatory elements that can be used alone or in combination with promoters. As used herein, "promoter" includes reference to a region of DNA upstream from the start of transcription and involved in recognition and binding of RNA polymerase and other proteins to initiate transcription.

A nucleic acid is hybridizable to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), and Sambrook, J. and Russell, W., Molecular Cloning: A Laboratory Manual, Third Edition, Cold Spring Harbor Laboratory Press, Cold Spring Harbor (2001).

The chimeric transcription factor used to induce gene expression has a hormone-binding domain from a steroid receptor. When the hormone-binding domain is bound by hormone, the transcription factor localizes to the cell nucleus. Thus the method includes a step of exposing the cell to an effective amount of a hormone that binds to the hormone binding domain of the transcription factor. The effective amount of hormone refers to an amount that results in observable transcription of the target genes above background levels.

Embodiments

The invention relates to the regulation of protein abundance in eukaryotic cells. It is exemplified herein with novel yeast cells having a GEV system developed using a protrophic, HAP1+S288c strain of yeast. (All strains described herein are shown in Table 1, below).

One aspect of the invention relates to targeted protein depletion in yeast. The proteins of interest have a modified degron sequence attached thereto. Generally, the modified degron sequence is at the initiator codon of the open reading frame (e.g., methionine in yeast). In an alternative embodiment, the modified degron sequence is at a site internal to and in frame with the open reading frame such that the target protein retains native or near-native activity. Upon adding hormone inducer to the medium, a protease is induced which cleaves the N-degron, leaving an N-end rule destabilizing amino acid exposed at the N-terminus so that the proteins are rapidly degraded by the process known as N-end rule degradation. In this aspect of the invention, a protease (e.g., TEV) is induced by a transcription factor (e.g., GEV) and the protease targets the proteins of interest so that the proteins are rapidly degraded by N-end rule degradation.

The inducible protein depletion method allows rapid, specific target protein degradation simply by making the system hormone-inducible using a modular transcriptional activator that has a hormone-binding domain as well as the DNA-binding domain and activator domain. As exemplified in the examples herein, the hormone was β-estradiol and the transcriptional activator was GEV. As exemplified herein, GEV induced the tobacco etch virus (TEV) protease which unmasks an N-degron to enable N-end rule degradation of a target gene driven by its native promoter and modified to contain a dormant N-degron. Thus the inducible protein depletion method has an advantage over the tet-off system, of resulting in a rapid elimination of the protein products of the regulated genes.

Another aspect of the invention relates to a chimeric transcription factor. One chimeric transcription factor for use in the method of the invention is the transcriptional activator GEV, which has three modular domains from different sources that function in hormone binding, DNA binding and activation. Transcriptional activators with alternative modular domains are also contemplated.

The contemplated transcriptional activators are useful to get effective target specificity. By replacing GEV's GAL4 DNA binding domain with a DNA binding domain from a non-yeast transcription factor (such as LexA) or from custom-designed zinc fingers that recognize DNA sequences not found in *S. cerevisiae*, the number of non-target genes induced or repressed will be lower than with GEV.

When constructing similar transcriptional activators with alternative components, the most specific activator will have a DNA binding domain that has high target DNA specificity and low enough affinity for binding DNA that the chimeric protein only binds to a single sequence of interest. For example, the DNA binding domain can be any other endogenous, rationally designed or engineered zinc finger domain (e.g., zinc fingers from endogenous mouse transcription factor zif268, 4-fingered rationally designed zinc finger 4Z, or any other engineered Cys2His2 zinc finger domain). Two embodiments of the engineered zinc finger domain are the ZEV and the 4ZEV transcription factors. In these embodiments, the DNA binding domain of GEV is replaced with an alternative DNA binding domain that recognizes a sequence that is either absent from or rare within the yeast genome. Zif268, the DNA-binding domain of ZEV, recognizes the sequence GCGTGGGCG (SEQ ID NO: 2) as well as many previously described similar sequences. 4ZEV was designed to recognize the 12-basepair sequence GCGGCGGAGGAG (SEQ ID NO: 3) which is not found in the yeast genome. Specificity determination predicts this zinc finger would function with all binding sites included in GCG(G/C)(C/G)(G/T)G(A/C)G(G/A/C)(A/C)(G/T) (SEQ ID NO: 4). In practice, the target sites for ZEV or 4ZEV are arranged as 3 dimer site targets (6-monomeric targets) with one or two bases between each monomeric target to allow for efficient assembly around the DNA double helix.

Since the transcription factors have a modular DNA-binding domain derived from other organisms or have a completely synthetic DNA-binding domain, the transcription factor and the inventive method are useful with respect to any eukaryotic cell.

With respect to other alternative modular domains of the transcription factor, the invention contemplates replacing the hormone binding domain so that a variety of hormones will work with the inventive system. In this case the hormone binding domain is replaced by the binding domain of any hormone receptor such that hormone binding results in nuclear localization of the transcription factor. For example the binding domains of the glucocorticoid or mineralocorticoid receptors may be used.

Replacement of the VP16 activating domain with other activating domains such as a protein sequence that provides an acidic region is also contemplated (e.g., the acidic regions of GAL4 or GCN4).

The ACT1 promoter used for driving GEV expression in the examples is a relatively strong promoter. While this is an advantage for some uses, a diversity of promoter strengths should be considered when constructing a system similar to what has been herein described but with alternative components. The diversity of promoter strengths is an important consideration, since very strong induction appears, from the data shown, to be at least partly responsible for the modest impairment of growth seen under full induction. This diversity of promoter strengths can be generated by isolating mutant promoters, or by using weaker natural promoters.

The contemplated invention includes a variety of promoters to express the GEV, ZEV or other hormone-activated transcriptional activator. Any promoter native to the organism in which the inventive system is placed (or that works by virtue of similarity in the original organism) is appropriate. The promoter should be constitutive, expressing the activator at an appropriate level such that, upon hormone treatment, the desired graded response of activation is achieved. In addition to ACT1 in yeast, other examples that exemplify this concept include the TDH3, ADH1, or *Ashbya gossypii* TEF promoter or, in mammalian cells, the cytomegalovirus promoter (CMV).

The inventive protein depletion system contemplates use of an alternative protease. In this respect, what is contemplated is use of any protease with a specific recognition sequence that is not present in any of the native proteins in the organism used in the depletion system. For example, the inventive protein depletion system is also contemplated with use of proteases 2A or 3C, encoded by the genome of human rhinovirus (HRV 2A, HRV 3C).

Another manner of constructing the system of the invention is by adapting other nuclear receptors that work by the same mechanism as the one in our GEV system, so that independent induction of two target genes can be accomplished. This will be particularly useful if one wants to use the system to provide pulses of protein. With two independent inducing systems one can induce synthesis of a target protein by adding one inducer, and then destroy, at will, the protein by inducing TEV with the other inducer.

The transformed cells can provide rapid depletion of single or multiple cellular proteins. This system is readily adaptable to the study of essential genes (genes that are lethal if deleted). Through rapid depletion, the cell's transcriptional response to the loss of these genes can be assayed over a time course using gene expression microarrays. Depletion via the degron method mimics the effect of application of potential inhibitors of a target polypeptide. Studies are conducted in relevant physiological conditions in the presence of normal or near normal expression of the target (before application of inhibitors). This enables determination of the immediate and/or long term effects of inhibition (depletion) to assess target and off-target physiological effects. This is especially useful if genetic deletion of the target leads to inviability. Likewise, transient induction can be assessed, starting from no expression, or normal expression (e.g., diploid cells with one normal and one hybrid transcription factor inducible (promoter-modified) target present).

Both induction and degradation are "tunable", facilitating comparative two-strain screens. Induction level adjustment is convenient for "rescue" screens, where overexpression would be deleterious to growth, or would affect another assay marker and compounds that inhibit the target return the cells to a normal state (i.e. growth or normal marker expression). When induction is undesirable but a two-strain comparative screen is indicated, partial depletion can be accomplished to enable comparison to cells with normal expression of the target.

The rescue screen is useful when the target protein is an enzyme or structural protein that, when overexpressed, is harmful to the cell (e.g., tubulin). The target of this screen is not necessarily native to the screening organism. For example, a mammalian target could be screened in yeast, as long as the harm (toxicity) of the screening cells is related to the manner the target functions in its natural host. In such a case, a target gene construct is prepared having a promoter responsive to the hormone-inducible activator and this is introduced into a chromosome of the cells of the screening organism. Growth studies are conducted to determine the level of hormone necessary to achieve a constant level of target protein that leads to a growth deficiency of the host organism. These host cells displaying the growth deficiency are then exposed to a compound library and a determination is made of which compound(s) afford a growth advantage to these host cells. The compounds that afford a growth advantage are candidates for enzymatic inhibitors or structural disruptors of the target protein.

Depletion of a protein involved in the production, processing or consumption of a valuable metabolite or protein can be accomplished in a near gratuitous fashion. Application of the depletion inducer at a strategic phase of batch fermentation can lead to increased yield of the desired metabolite or protein.

Thus this system has applications in synthetic biology, pharmaceutical and agricultural industries, and in basic biomedical research. One application is in bioengineering for biologic or compound synthesis. This system can be integrated as a module into engineered circuits. As used herein, a circuit is a programmed set of genes being expressed, or proteins that are degraded. Rapid, gratuitous degradation of a single protein is used in the construction of more complex, synthetic circuits that are orthogonal to the cell's wild type machinery. For example, the modified yeast cells are used as a vehicle for producing large amounts of a particular chemical, since achieving specific levels of particular proteins is essential for achieving maximal efficiency. The GEV/TEV system allows a particular target protein to be tuned down without affecting the other cellular machinery.

The cells of the invention are also useful for high throughput screening (HTS) of compound libraries by exposing these compound libraries to the protein-depleted cells by methods well known to those skilled in the art. HTS can, for example, be used for discovery of new pharmaceutical or agricultural compounds. The cells used in this manner behave essentially as wild type capable of growing in normal, non-physiologically-changing medium. They allow for target identification.

For some drug targets, constitutive overexpression or elimination of a target protein is not possible because this would produce deleterious consequences for the cell. Thus, a screen of the type that uses a control strain and a modified strain (or cell line) for testing compounds would not be possible. The protein induction/depletion system of this invention overcomes that problem. With this system it is possible to transiently overexpress or deplete a target. In doing so, one skilled in the art can 1) determine the appropriate duration and concentration of exposure to the hormone used for induction or depletion, so that the target protein concentration is sufficiently changed for the purpose of the assay, 2) expose cells to the library of compounds, 3) determine the appropriate time for cells to recover from the perturbation (e.g. after dilution with non-hormone containing medium) and 4) determine the growth difference, or other assay-specific change, conferred by a compound, that distinguishes the treated control cells from the hormone responsive cells.

The following examples set forth the general procedures involved in practicing the present invention. To the extent that specific materials are mentioned, it is merely for purposes of illustration and is not intended to limit the invention.

Materials And Methods

Strains:

Prototrophic HAP1+ yeast strains were constructed that can be readily modified to either (1) induce expression of a single gene or (2) rapidly degrade a single target protein (Table 1, below). These strains contain an integrated copy of GEV driven by an ACT1 promoter and are gal4Δ gal1Δ.

For induction/overexpression studies, GEV-containing strains of either mating type: DBY12020 (MATa) and DBY12021 (MATα) were constructed. These strains can be transformed with a KanMX-$P_{GAL1}$ linear fragment (Liko et al., 2006) in front of any non-essential gene to make that gene inducible by β-estradiol.

For protein degradation studies, DBY12132 and DBY12200 were constructed, which contain both GEV and the TEV protease. In DBY12132 and DBY12200, $P_{ACT1}$-GEV is at the LEU2 and CAN1 locus, respectively. By modifying a target gene in these strains to contain a degron sequence recognized by TEV at its amino terminus, a gene can be expressed under its native promoter and degraded in the presence of β-estradiol.

Media and Growth Conditions:

For microscopy and flow cytometry experiments, cells were grown in low-fluorescence media (LFM). LFM is chemostat minimal medium (BRAUER et al. 2008) lacking riboflavin and folic acid, and contains, in addition to glucose (20 g/L), 5 g/L $(NH_4)_2SO_4$, 1 g/L $KH_2PO_4$, 0.5 g/L $MgSO_4$, 0.1 g/L NaCl, 0.1 g/L $Ca_2Cl$, 0.5 mg/L $H_3BO_4$, 0.04 mg/l $CuSO_4$, 0.1 mg/l KI, 0.2 mg/l $FeCl_3$, 0.4 mg/l $MnSO_4$, 0.4 mg/l $MnSO_4$, 0.2 mg/l $Na_2MoO_4$, 0.4 mg/l $ZnSO_4$, 2 ng/l biotin, 0.4 mg/l calcium pantothenate, 2 mg/l inositol, 0.4 mg/l niacin, 0.2 mg/l para-aminobenzoic acid, 0.4 mg/l pyridoxine HCl, 0.4 mg/l thiamine.

For induction experiments, yeast were cultured in 500 mL chemostats (Sixfors; Bottmingen, Switzerland) under phosphate-limitation (20 mg/L potassium phosphate) and pulsed with 1 μM β-estradiol (Tocris Biosciences; Missouri). For the MET4 induction experiment, phosphate-limited media was supplemented with 200 mg/L methionine. Culture volume was maintained at 300 mL. 12-18 hours of batch phase growth prior to pump turn-on was initiated from a 1/60 dilution of cells grown overnight in the same medium. Cultures were grown at 30° C., stirred at 400 RPM, and aerated at 5 L/min with filtered humidified air.

For all other experiments, cells were grown on rich medium (YPD; 2% peptone, 1% yeast extract).

Microscopy:

Fluorescence was measured with an epifluorescence Nikon Eclipse-TI inverted microscope using a Nikon 40×/0.95NA DIC Plan Apo objective. The microscope is equipped with a PerfectFocus system (Nikon) for maintaining the correct focal plane, a Clara CCD Camera (Andor DR328G) for recording fluorescence emission, and a TI-S-ER motorized stage with encoders to ensure near perfect return to marked stage positions (Nikon MEC56100). GEV-GFP emission was visualized at 525 nm (50-nm bandwidth) upon excitation at 470 nm (40-nm bandwidth) (Chroma #49002_Nikon ETGFP filter cube). HTB2-mCherry emission was visualized at 620 nm (60-nm bandwidth) upon excitation at 545 nm (30-nm bandwidth) (Chroma #96364_Nikon ET-DSRed filter cube). Image acquisition was automatically controlled using NIS Elements software.

For Fluorescence in situ hybridization (FISH), images were acquired with an Olympus IX81 inverted fluorescence microscope as described in Silverman et al. (2010).

GEV-GFP Localization Experiment:

Overnight cultures of DBY11415 (MATa/MATα HTB2-mCherry-caURA3/HTB2 his3/HIS3, (gal1+$P_{GAL10}$):: loxP/

GAL1, gal4::LEU2/GAL4, HAP1+/hap1−, leu2Δ0::P$_{ACT1}$-GEV-GFP-KanMX/LEU2) were grown in LFM overnight to saturation. Overnight cultures were diluted 1:50 in fresh LFM media to a Klett of ~10. The Klett was monitored, and at Klett 40 cells were loaded into 96-well glass-bottomed optical plates for microscopy (Nunc #265300). Each well in the 96-well plate was incubated with 30 ul of concanavalin A solution (2 mg/ml concanavalin A MP Biomedicals #150710 dissolved in 5 mM MnCl$_2$ 5 mM CaCl$_2$ pH 6.5) to fix cells to the bottom of the plate. After a 5 minute incubation, excess concanavalin A was aspirated off, and 4 μL of cell culture+91 μL of fresh LFM media+1 μL of 100% ethanol were added to each well. Cells were allowed to settle to the bottom of each well while stage positions were marked on the microscope using ambient room light.

Cells were imaged immediately prior to and immediately after addition of 4 μL β-estradiol to each well. Each experiment was done in triplicate and two images were taken per each well of the 96-well plate, resulting in 6 image frames per concentration of β-estradiol. Images were acquired every 170 seconds during induction of GEV-GFP localization.

GEV-GFP Washout Experiment:

Growth of strain DBY11415 was performed as described above for the GEV induction experiments. Cells were maintained in a flow cell (Bioptechs FCS2) during microscopy. Cells were adhered to the bottom of a 40 mm round coverslip by first incubating the coverslip with concanavalin A (as above) and then the coverslip was assembled into the FCS2 chamber. Cells were maintained at room temperature during the course of the experiment (25° C.). The Klett of the culture was 110 when cells were loaded into the flow cell. Two peristaltic pumps (INSTECH P720) were used to perfuse media to cells during microscopy. One pump perfused LFM medium and the other perfused LFM media with 1 μM β-estradiol. The pump flow rates were automatically controlled by computer (Bioptechs Perfusion Controller) and by switching between pumps media was exchanged within the cell chamber in ~2 minutes. GEV nuclear localization was first induced with LFM+1 uM β-estradiol for 50 minutes. The pump flow rates were then switched and images were acquired every 300 s to monitor delocalization of GEV-GFP. Conditions for imaging GFP and mCherry were identical to the induction experiment except that a 1.5× optovar was inserted into the optical path to magnify images from 40× to 60×.

Microscopy Image Processing:

Image processing was performed by preprocessing the images in ImageJ and then using a custom written Matlab script to extract the intensities in the nuclei relative to the cytoplasm. Briefly, the image processing was done as follows: Fluorescence images were background subtracted using the rolling ball background subtraction command in ImageJ using a ball radius of 50 pixels. The method has been previously described (STERNBERG 1983). Images were examined by eye in ImageJ and out of focus images were removed before further analysis.

These preprocessed images were then analyzed using a custom-written Matlab script. In brief, the code first identifies cells using various thresholding commands on the GFP images to create a "mask" of the image (an image where pixels inside of cells are identified as 1 and pixels outside of cells are identified as 0). The user is then given an opportunity to correct any errors in this mask by hand. The code then uses similar thresholding commands on the mCherry image to identify cell nuclei and create a mask for the nuclei. Using these two masks the script then extracts intensity information from the GFP image for each cell identified in the cell mask, using the nucleus mask to differentiate between the cytoplasm and the nucleus. A particle tracking routine (track.m) is then used to align values for cells and nuclei between images taken at different time points. Finally, the various parameters are exported as cell by time matrices where each row represents a single cell identified throughout the time course. The localization score in all figures is determined for each cell by first averaging the top 5% of pixel intensities and then dividing this number by the average pixel intensity over the entire cell (CAI et al. 2008).

Flow Cytometry:

Cell fluorescence was measured with a BD LSRII Multi-Laser Analyzer with HTS. "High-fluorescence" in single cells was determined from the distribution of fluorescent intensities in cells lacking GFP (the distribution is determined from the fluorescent values of 100,000 cells). The cutoff for "high-fluorescence" was set at the top 0.2% of the distribution (GFP signal=190 au).

Fluorescence In Situ Hybridization:

FISH probe design and experiments were performed as described by Silverman et al. (2010). DBY12040 was grown to early-log phase and pulsed with 1 μM β-estradiol. Cells were fixed prior to β-estradiol addition to the culture, and at 2 and 8 minutes (FIG. 3B) following β-estradiol addition. The Cy3-labeled DNA probes used for FISH are listed in Table 2, below.

Growth Curves:

100 μL of cells+media were grown on flat-bottom 96-well plates (Costar #3631). A$_{600}$ was measured every 15 minutes in a Synergy HT (Biotek; Vermont) microplate reader. Cells were grown at 30° C. with medium shaking. Growth rates were computed with spline-fits using the grofit R package (KAHM et al. 2010).

Microarrays and Functional Annotation:

RNA from cells was extracted, labeled, and hybridized to Agilent expression microarrays as described by (Brauer et al., 2008) with slight modifications. Briefly, RNA was extracted from frozen cells with a standard acid-phenol method and then cleaned with RNeasy (Qiagen). Cleaned mRNA was then converted to cDNA and subsequently converted to labeled cRNA with the Agilent Quick-Amp Labeling Kit (Part No. 5190-0424). Microarray hybridizations were performed for 17 hours at 65° C. and rotated on a rotisserie at 20 RPM. Microarrays were washed and then scanned with Agilent Feature Extractor Software version 9.5. Flagged features marked as unreliable were marked N/A. Raw green- and red-channel intensities were floored to a value of 350 (i.e., intensities below 350 were set equal to 350). If the numerator (red-channel, sample RNA) for a given measurement was floored, the denominator (green-channel, reference RNA) for that measurement was set to the average green channel intensity for that gene. The purpose of this smoothing process is to make genes with negligible red-channel signal intensity less sensitive to small fluctuations in the reference intensity. After flooring of the data, the log 2 ratios were computed.

For time series experiments, 5 mL of cells were taken per culture per time point. Reference RNA was taken from DBY12001 grown in a phosphate-limited chemostat at a dilution rate of 0.18 h$^{-1}$. Enrichment for gene ontology (GO) terms was determined using GO-term finder (Boyle et al., 2004).

Construction of the Degron System:

This consists of two parts, each of which ends up inserted into the chromosome. One of these is the protease cassette, which contains the GAL1 promoter, a modified TEV protease-coding region, the spliceosome subunit p14 peptide, a CYC1 terminator, and a selectable (hygromycin) marker, all integrated to replace the genomic GAL1 coding sequence.

The details of this construction are described in detail below. The second part is a simple way to insert the degron/marker cassette at any promoter of interest. To this end, a generic template was constructed for PCR that enables the placement of the modified degron/marker cassette at the initiator methionine codon of any open reading frame; the details are also to be found below.

Modification of Target Genes to Make them TEV-Sensitive:

Since native proteins are not sensitive to the TEV protease, a generic system was devised to make the required modifications of any gene routine. The overall idea is to generate a native promoter-driven degron-modified gene. A particular new feature of this method is the inclusion of a removable (CRE-LOX) segment that results in loss of the selectable marker. The details of this construction, and its application to the specific cases of MET4 and MET31 are given below.

Construction of can1Δ::$P_{ACT1}$-GEV Strains:

The ~2,240 bp $P_{ACT1}$-GEV construct was amplified from the pAGL plasmid (Veatch et al., 2009) using oligonucleotides containing 56-59 bases of sequence identity to the flanking region of the CAN1 gene (ACT1-GEV_to_CAN1 FOR and ACT1-GEV_to_CAN1 REV). This PCR product was then transformed into either MATa or MATa wild type prototrophic yeast cells using a standard protocol.

Western Blots:

Total protein was extracted from ~10 mL aliquots of cultures at ~2×10$^7$ cells/mL using YPX extraction kit (Protein Discovery, Knoxville, Tenn.) with the addition of protease inhibitors (Roche tablets, cat#11836170001). Proteins were separated using Invitrogen NuPage precast 10% Bis-Tris gels and transferred to Invitrolon PVDF (Invitrogen cat#LC2005) according to the manufacturer's protocols. Primary antibody for the β-Myc epitope was mouse anti-human c-Myc from BD Pharmingen (cat#51-1485GR). Secondary antibody was goat anti-mouse-HRP (cat#115-035-003) from Jackson ImmunoResearch. Primary antibody dilution was typically 1/1000 and secondary antibodies were used at 1/10,000 dilution. Immunoreactive peptides were detected by incubation with ECL$^+$ detection reagent (Amersham/GE RPN2132) and imaging on HyBlot CL autoradiography film (Denville Scientific, Metuchen, N.J.). As a loading control, blots were probed with mouse monoclonal anti-β-Actin antibody loading control cat#ab8224, Abcam, Cambridge, Mass. (1/600 or 1/2000). Secondary antibody was as above, goat anti-mouse-HRP. Protein levels were quantified with the "Gel Analysis" feature in ImageJ and normalized to the t=0 levels in each time course.

GEV Strain Constructions:

Primers are listed in Table 3, below. DBY12021 was constructed through a series of crosses and sporulations. First, UCC1909 was crossed with DBY12013 (ura3Δ0 leu2Δ0 lys2-1280 HAP1+Matα) and sporulated to generate DBY11191 (ura3Δ0 leu2Δ0::$P_{ACT1}$-GEV-NatMX met15:: LYS2 lys2-hap1-Mata). RSMx2-10a was then crossed with DBY12017 ((Pgal10+gal1)::loxP $P_{GAL1}$-CRE-phleo HAP1+ Matα) and sporulated to generate DBY12018 (($P_{GAL10}$+ gal1)::loxP leu2Δ0::$P_{ACT1}$-GEV-NatMX HAP1+Mata) and DBY12019 (($P_{GAL10}$+gal1)::loxP leu2Δ0::$P_{ACT1}$-GEV-NatMX HAP1+Matα). A gal4::LEU2 linear DNA fragment was PCR amplified from UCC1864 and transformed into DBY12018 and DBY12019 to generate the protrophic strains DBY12020 (($P_{GAL10}$+gal1)::loxP leu2Δ0::$P_{ACT1}$-GEV-NatMX gal4Δ::LEU2 HAP1+Mata) and DBY12021 (($P_{GAL10}$+gal1)::loxP leu2Δ0::$P_{ACT1}$-GEV-NatMX gal4Δ:: LEU2 HAP1+Matα).

The C-terminus-tagged GEV-GFP reporter was generated by homologous recombination of GFP-KanMX from pFA6-GFP-KanMX (Sheff and Thorn, 2004) into DBY12021. The primers used for making the amplified GFP-KanMX are GEVGFP-F and GEVGFP-R.

The C-terminus-tagged HTB2-mCherry fusion was generated by homologous recombination. mCherry was first digested from pFA6a-mCherry-HIS3MX6 (pKT355, with PacI and AscI. pKT175 was cut with PacI and AscI to remove YECitrine. The digested mCherry was ligated into the pKT175 backbone. The primers used for making the mCherry-CaUra3 PCR fragment for transformation are HTB2-F and HTB2-R (Table 3, below).

The strains DBY12027, DBY12040, and DBY12086 were made by homologous recombination of KanMX-$P_{GAL1}$ DNA into DBY12021. KanMX-$P_{GAL1}$ DNA was PCR amplified from DBY11408 and with extra homology to insert directly upstream of the target ORF.

Insertion of TEV Protease at the GAL1 Locus:

We deleted the chromosomal GAL1 ORF, replacing it with the TEV protease. To do this, two overlapping PCR products were created. The first PCR product was generated using oligonucleotides homologous to 1) the GAL1 promoter and to 2) the CYC1 terminator, using pCT271 (which contains $P_{GAL1}$-TEV-CYC1 (Taxis et al. 2009)) as a template. The second PCR product was generated using one oligonucleotide comprising 40 nt at the end of the CYC1 terminator sequence (for overlap with the first PCR product) followed by the TEF promoter sequence, paired with a second oligonucleotide comprising 40 nt downstream of the GAL1 ORF followed by TEF terminator sequences, using pAG32 as a template (Goldstein and McCusker, 1999). The two PCR products were transformed into strain DBY11389, selecting for hygromycin B (Calbiochem) resistance, to generate the gal1Δ::TEV-HphMX strain. For some experiments, this TEV allele was modified to replace the HphMX cassette with the URA3 gene. To do this, two oligonucleotides were used to PCR URA3 from the pAG26 template (Goldstein and McCusker, 1999): 1) containing the CYC1 terminator sequence in the TEV construct and the URA3 promoter present in pAG26 and 2) containing the URA3 terminator and a sequence 3' of the gal1Δ::TEV-HphMX insertion. This PCR product was transformed into strain DBY12096, resulting in strain DBY12132. All oligonucleotides are listed in Table 3, below.

Construction of a Generic Plasmid Template for NDeg-Gene Specific PCR Product Generation:

Plasmid pCT251 (Taxis et al., 2009) was used as a template for PCR to generate a fragment with 40 bp of homology to a region preceding the EcoRI site of YCplac33, an ATG, the coding sequence of the degron cassette starting with the first spacer sequence (encoding SISTL ... (SEQ ID NO: 5)) and ending with the ATG at the terminus of the last spacer region ( ... ENSSM (SEQ ID NO: 6)) followed by 40 bp of homology to the YCplac33 sequence region following the EcoRI site ("overlap tipi to ycplac F"; "overlap tipi to ycplac R"). YCplac33 was cleaved with EcoRI and was used, in conjunction with the PCR fragment above, to transform a ura3 auxotroph of yeast (DBY12015) to Ura prototrophy. The resulting plasmid (pRB3324) was reconstructed by homologous recombination in yeast, and recovered into E. coli by standard methods (Ma et al., 1987).

Figure 15:
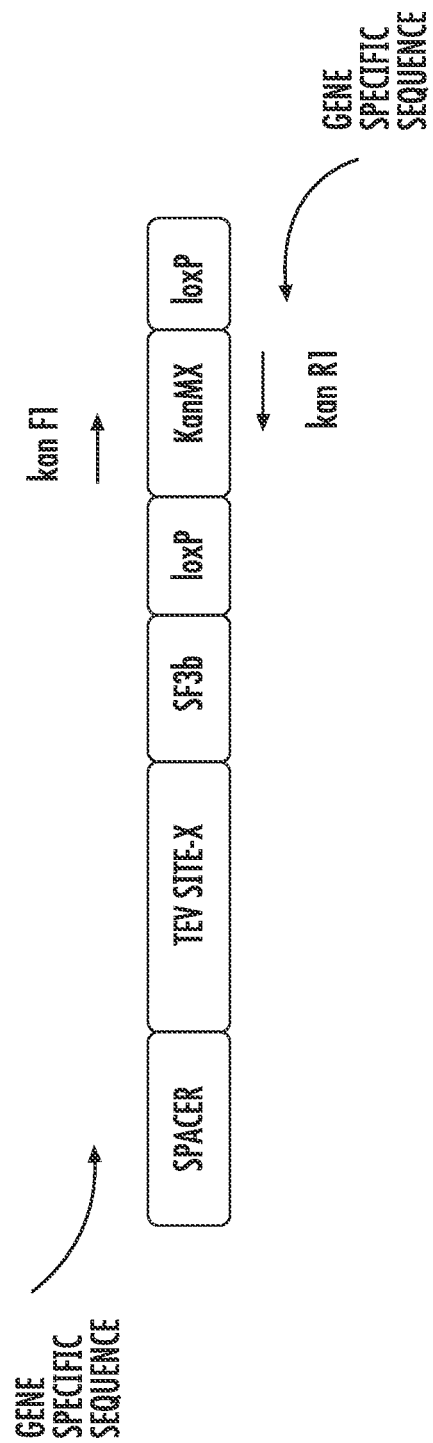
FIG. 15: Strategy for generating PCR products for integrating TDeg'F at the ATG of the gene of interest. kan F1 and kan R1 are fixed sequences that can be used for all PCRs. Two gene-specific oligonucleotides are constructed with homology to the loxP sites and sequence overlap around the ATG of the target gene. The reverse primer is designed to be in frame with the loxP encoded ORF. Gene specific primers can be used together. Alternatively, the forward primer is used in conjunction with kan R1, and the reverse primer is used with kan F1.
Figure 16:
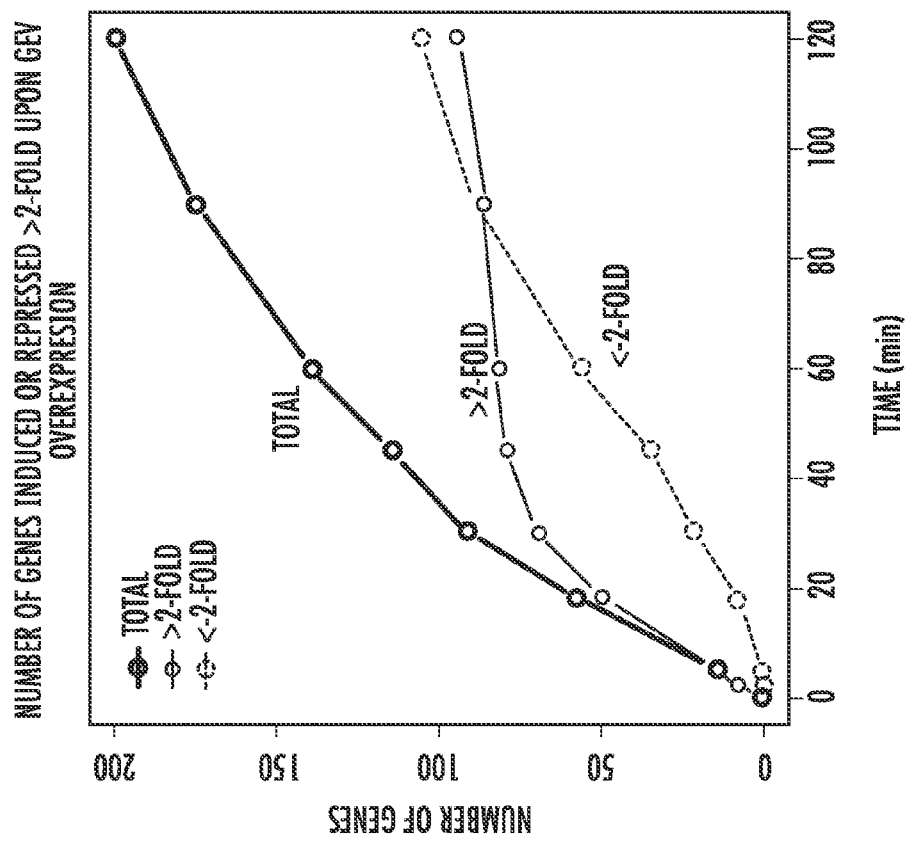
FIG. 16: The number of genes that are induced or repressed >2-fold via GEV overexpression in DBY12021. These values were computed from the microarray data shown in FIG. 6.

The spacer region after the SF3b coding sequence of the degron cassette derived from pCT251 contains two EcoRI sites. To replace this sequence with the loxP-flanked KanMX marker we used plasmid pUG6 (Guldener et al., 1996) as a template to generate two PCR products (necessary because of the identity of the loxP sites). The first product was generated by using an oligonucleotide ("N-deg F+lox F") that contains 40 nt of homology preceding the first (most amino-terminal-encoding) EcoRI site of pRB3324 and 20 nt of homology to the 5' loxP site of pUG6, in conjunction with an oligonucleotide (KanMX r1) homologous to a sequence of KanMX near the 3' end. The second product was generated using an oligonucleotide (KanMX f1) homologous to a sequence near the 5' coding sequence of KanMX in conjunction with an oligonucleotide ("N-deg R lox R") containing 40 nt of homology to the second (most carboxyl-encoding) EcoRI site of pRB3324 and 20 nt of homology to the 3' loxP site of pUG6. Plasmid pRB3324 was cut with EcoRI and used with the two oligonucleotides described above to transform yeast cells selecting for kanamycin (G418 sulfate; Cellgro) resistance. The resulting plasmid, pRB3326, recovered by transformation of the yeast DNA into E. coli, is a generic template for generating PCR products for insertion at the initiator methionine of any yeast gene. FIG. 15 shows the NDeg sequence that results from Cre-mediated loxP recombination of such a construct at any gene.

NDeg-MET4 Construction:

To generate chromosomal NDeg-MET4, the following oligonucleotides were used: 1) an oligonucleotide (MET4-Tipi-F) comprising 40 nucleotides of homology to the sequence upstream, and including, the ATG of MET4, and 20 nucleotides encoding the first spacer amino acids at the start of the degron construct of pRB3326; and 2) an oligonucleotide (MET4-Tipi-R) comprising 40 nucleotides of homology to the sequence downstream of the ATG (including an additional ATG) and 20 nucleotides of the loxP-modified spacer sequence at the end of the degron construct. This PCR product was used to transform a diploid (DBY12021/DBY12032) to kanamycin resistance. After recovery and verification of the clone containing this construct, we transformed the strain with pSH65 (Gueldener et al., 2002) containing a GAL1-promoter driven Cre recombinase, selecting for resistance to phleomycin (Invivogen). The strain was grown overnight in galactose-containing medium and plated for single colonies on YPD medium. The resulting colonies were screened for kanamycin resistance and the sensitive clones were PCR-verified to have lost the loxP-KanMX cassette. The strain was sporulated and haploids selected for epitope tagging.

Wild type and the corresponding NDeg-MET4 strains were transformed with a PCR product to insert 13-Myc epitopes at the MET4 carboxyl terminus pFA6a-13Myc-KanMX6 (Longtine et al., 1998) was used as a template for oligonucleotides (MET4-Myc-F and MET4-Myc-R) containing sequences adjacent to the stop codon of MET4 and in-frame 13Myc sequence (5' primer) or TEF terminator sequences (3' primer). The resulting PCR fragment was transformed into cells selecting for kanamycin resistance. Standard genetic crosses were performed to generate DBY12055 and DBY11440.

NDeg-MET31 Construction:

MET31 was modified in a similar fashion to that of MET4. Oligonucleotides for MET3'-specific NDeg amplification were Met31-TIPI-F and Met31-TIPI-R. The PCR product was used to transform a diploid to Kanamycin resistance. The KanMX sequence was eliminated as above. After sporulation both wild-type MET31 and NDeg-MET31 haploid strains were recovered. Carboxy-terminal 13-Myc tags were appended to the sequence of each variant as above. Diploids were generated to contain GEV, TEV and each of the MET31 variants (DBY12234, NDeg-MET31-13Myc; DBY12235, MET31-13Myc) for protein extraction.

β-Galactosidase Activity Assay:

Assays were performed essentially as described in (Liu et al., 1999) with minor modifications. 5 mL of cells transformed with pCM64-GAL1 were grown to midlog phase in SC-URA medium at 30° C., then incubated at indicated temperatures for the indicated times with or without (a) 5 µL of ethanol (vehicle control), (b) 2 µL of 2.5 mM β-estradiol (Sigma) dissolved in ethanol (final concentration of 1 µM), (c) 5 µL of 1 mM DOC (deoxycorticosterone; Sigma) dissolved in ethanol (final concentration of 1 µM), or (d) 5 µL of 10 mM DOC dissolved in ethanol (final concentration of 10 µM). Cells (1 mL) were harvested by centrifugation, washed once with sterile $H_2O$, and resuspended in 700 µl of Z buffer (100 mM sodium phosphate, pH 7.0, 10 mM KCl, 1 mM $MgSO_4$, 50 mM β-mercaptoethanol). 50 µl of chloroform and 50 µl of 0.1% SDS were added, and the cell suspension was vortex-mixed at top speed for 30 seconds followed by addition of 200 µl of 4 mg/ml ONPG (ortho-nitrophenyl-β-galactoside; Sigma) was added to each sample and incubated at room temperature until pale yellow color appeared. 350 µl of 1 M $Na_2CO_3$ was added to stop the reactions. After clarification by centrifugation, the supernatant was diluted, and $A_{420}$ was measured within the linear response range. Specific β-galactosidase activity was calculated as follows: $(A_{420} \times 1000)/(A_{600} \times (\text{volume of cells examined in ml}) \times (\text{time of incubation in minutes}))$ and reported in Miller units.

pCM64-GAL1 Plasmid:

pCM64-GAL1 (University of Texas Health Science Center at Houston; K. Morano) was constructed by inserting the promoter region of GAL1 in front of truncated lacZ into the plasmid pCM64, which was derived from pLG669Z (Guarente and Ptashne, 1981).

Engineered Cys2His2 Zinc Fingers:

The creation of the ZEV system was accomplished by replacing the gal4 DNA binding domain of the original GEV system with a set of Cys2His2 Zinc fingers. The ZEV system utilizes the zif268 zinc fingers. The 4ZEV system uses the four zinc finger protein rationally designed below.

Sequences Used In Constructing ZEV And 4ZEV

Zif268:
GTRPYACPVESCDRRFSRSDELTRHIRIHTGQKPFQCRICMRNFSRSDHLTTHIRTH
TGEKPFACDICGRKFARSDERKRHTKIHTG (SEQ ID NO: 7)

4Z:
GTRPYACPVESCDRRFSRHANLTRHIRIHTGQKPFQCRICMRNFSRNANLVRHIRT
HTGSQKPFQCRICMRNFSRKADLRRHIRTHTGEKPFACDICGRKFARKGDLKRHT
KIHTG (SEQ ID NO: 8)

Optimal Zif individual target: GCGTGGGCG (SEQ ID NO: 2)

Alternative Zif targets with reduced affinity:
GCGTGGGTG (SEQ ID NO: 9)-2-fold reduction in affinity in comparison to optimal
GCGTGGGAG (SEQ ID NO: 10)-5-fold reduction in affinity in comparison to optimal Sequences Used In Constructing ZEV And 4ZEV GCGTGGG<u>C</u>C (SEQ ID NO: 11)-10-fold reduction in affinity in comparison to optimal
GCGTGGG<u>G</u>G (SEQ ID NO: 12)-20+ fold reduction in affinity in comparison to optimal
(Affinity differences from Miller J and Pabo CO (2001) J. Mol. Biol., 313, 309-315).

Zif in vivo target:
<u>GCGTGGGCGt GCGTGGGCGg GCGTGGGCGt GCGTGGGCGg GCGTGGGCGt GCGT
GGGCG</u> (SEQ ID NO: 13)

4Z designed optimal target: GCGGCGGAGGAG (SEQ ID NO: 3)

4Z in vivo target:
<u>GCGGCGGAGGAGTGCGGCGGAGGAGGAGCGGCGGAGGAGTGCGGCGGAGG
AGGAGCGGCGGAGGAGTGCGGCGGAGGAG</u> (SEQ ID NO: 14)

ZEV and 4ZEV Systems:

To test the optimal zinc finger –EV fusion and binding site complement, three linkers between the zinc fingers and the estrogen receptor were tested (5, 10 and 15 amino acids). These constructs were tested for their activity with a mCherry reporter when binding sites were positions, spacing and orientations. Ultimately it was found that the 5 amino acid linker used in conjunction with three pairs of binding sites placed head to tail, with a single base separating each site, was the most active combination. All further binding sites and zinc finger constructs were built according to this template.

Figure 18:
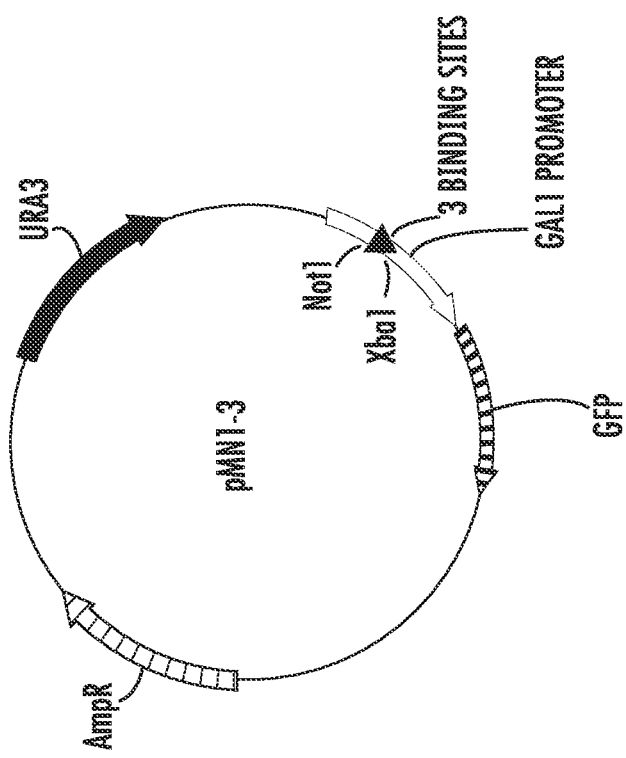
FIG. 18: Reporter Plasmids. The 3 canonical GAL4 binding sites have been removed and replaced with either three GAL4 binding sites, three ZEV binding sites, or three 4ZEV binding sites between Xba1 and Not1 restriction sites.
Figure 19:
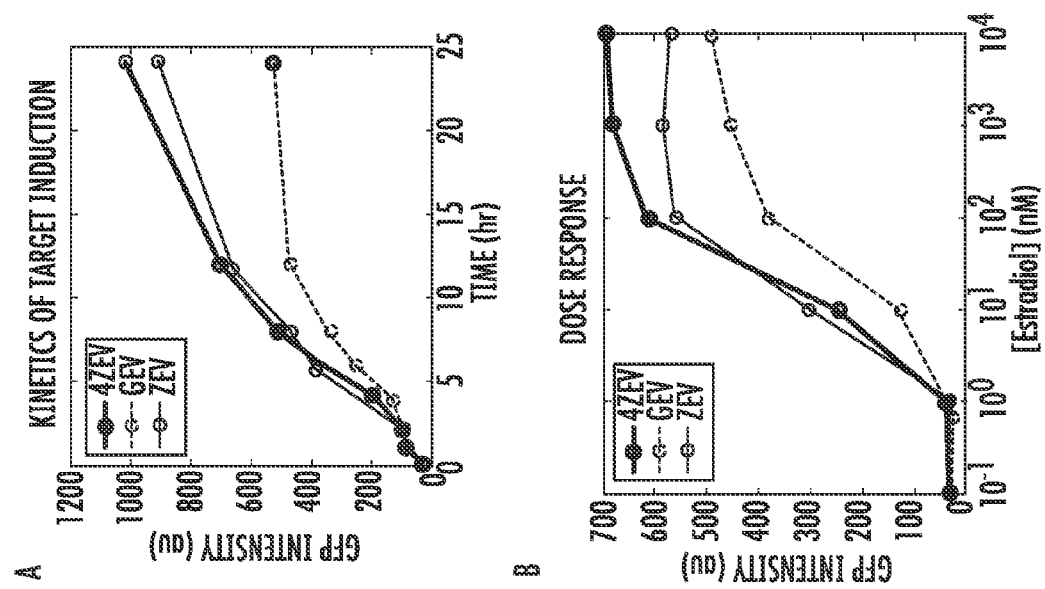
FIG. 19: (A) Kinetics of induction of reporters. (B) Dose response of reporters.
Figure 20:
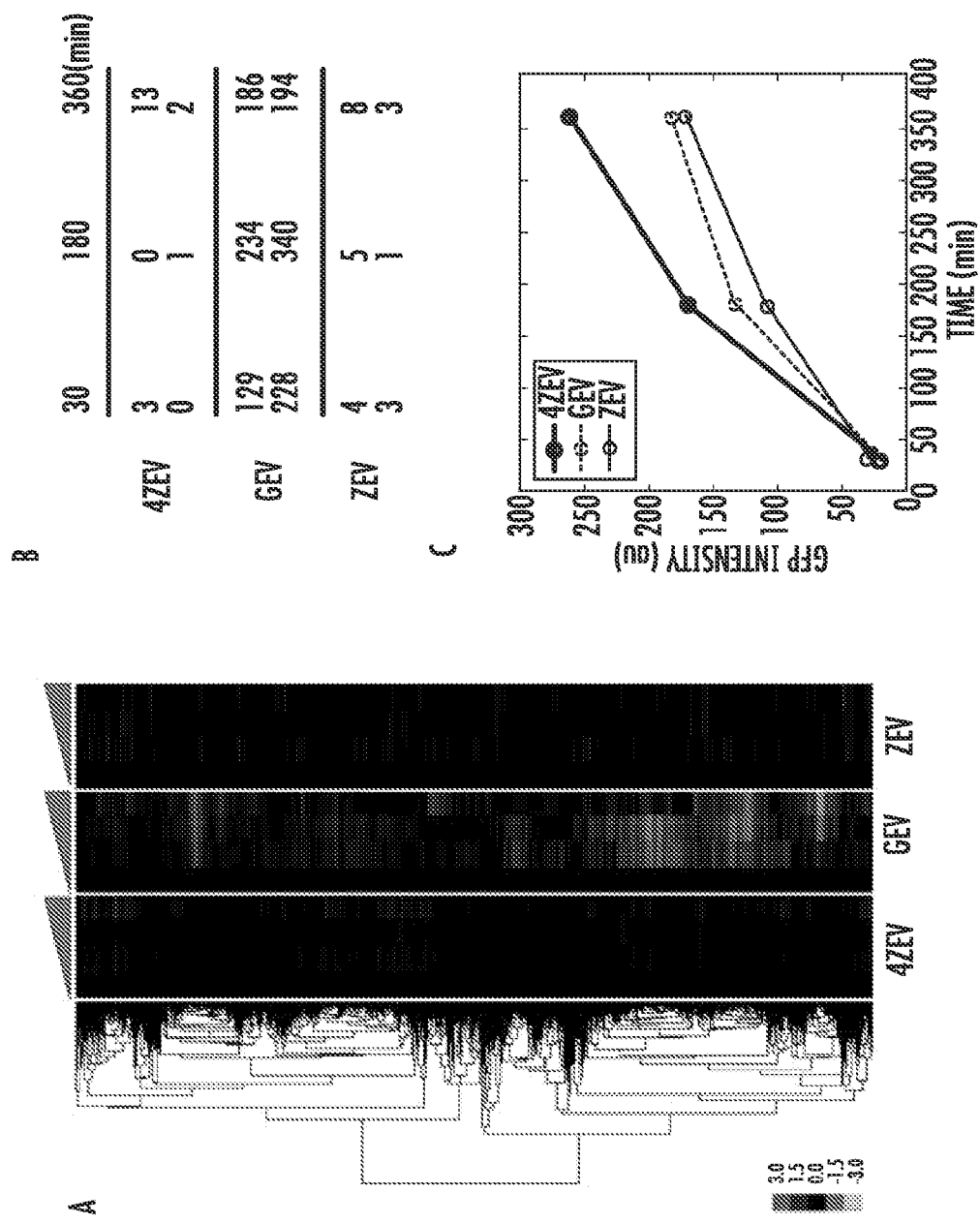
FIG. 20: (A) Expression response to the three expression systems at t=0, 30, 180, and 360 min. (B) The number of genes turned on by the respective "xEV"s at each of the 3 indicated time points. Indicated are the number of genes induced >2-fold (top row) and repressed >2-fold (bottom row) by each of the systems. (C) Induction of the appropriate reporter from strains in (A).

Construction of GFP Reporters:

GFP reporter plasmids were constructed to test the ability of the new ZEV and 4ZEV transcription factors to activate a target gene in the presence of the hormone β-estradiol. Reporter plasmids were constructed using the CEN plasmid pRS416 (Sikorski and Heiter 1989), which contains a URA3 selectable marker, as a template. A DNA fragment containing a modified GAL1 promoter fused to GFP (Gal1pr-GFP) was cloned into pRS416 between the NheI and AscI restriction sites. The GAL1 promoter was modified so that the 3 primary Gal4p (and also GEV) DNA binding sites were removed and replaced with DNA sequences containing 3 pairs of GEV, ZEV, or 4ZEV binding sites between the XbaI and NotI restriction sites (FIG. 18).

EXPERIMENTAL RESULTS

Example 1

The GEV System:

Two isogenic strains of opposite mating type were constructed to use for studies of gene induction/overexpression (DBY12020, DBY12021) studies in S. cerevisiae (see Materials and Methods). These strains contain an integrated copy of $P_{ACT1}$-GEV, so that GEV is produced constitutively and at relatively high levels. A gene placed immediately downstream of a GAL-regulated promoter will only be expressed after addition of β-estradiol to the growth medium (FIG. 1).

Importantly, though GEV binds DNA via a Gal4p DNA binding domain, it is not subject to inhibition or repression by glucose, making feasible induction and overexpression experiments in standard glucose-containing media simply by the addition of the inducer β-estradiol.

Example 2

Quantitation of GEV Localization

A chromosomally integrated C-terminus-tagged GEV-GFP reporter was constructed, and its localization was measured following pulses of β-estradiol (FIG. 2A) in single cells, using a microfluidic device (Hersen et al.; 2008; McClean et al., 2011). GEV localization level was proportional to the amount of added β-estradiol for a range of concentrations. At the higher doses (100 nM to 10 μM), nuclear localization signal is seen emerging from the background about 6-8 minutes following hormone addition. The initial rate of localization achieved its maximum at concentrations at or above 1 μM β-estradiol.

Figure 2:
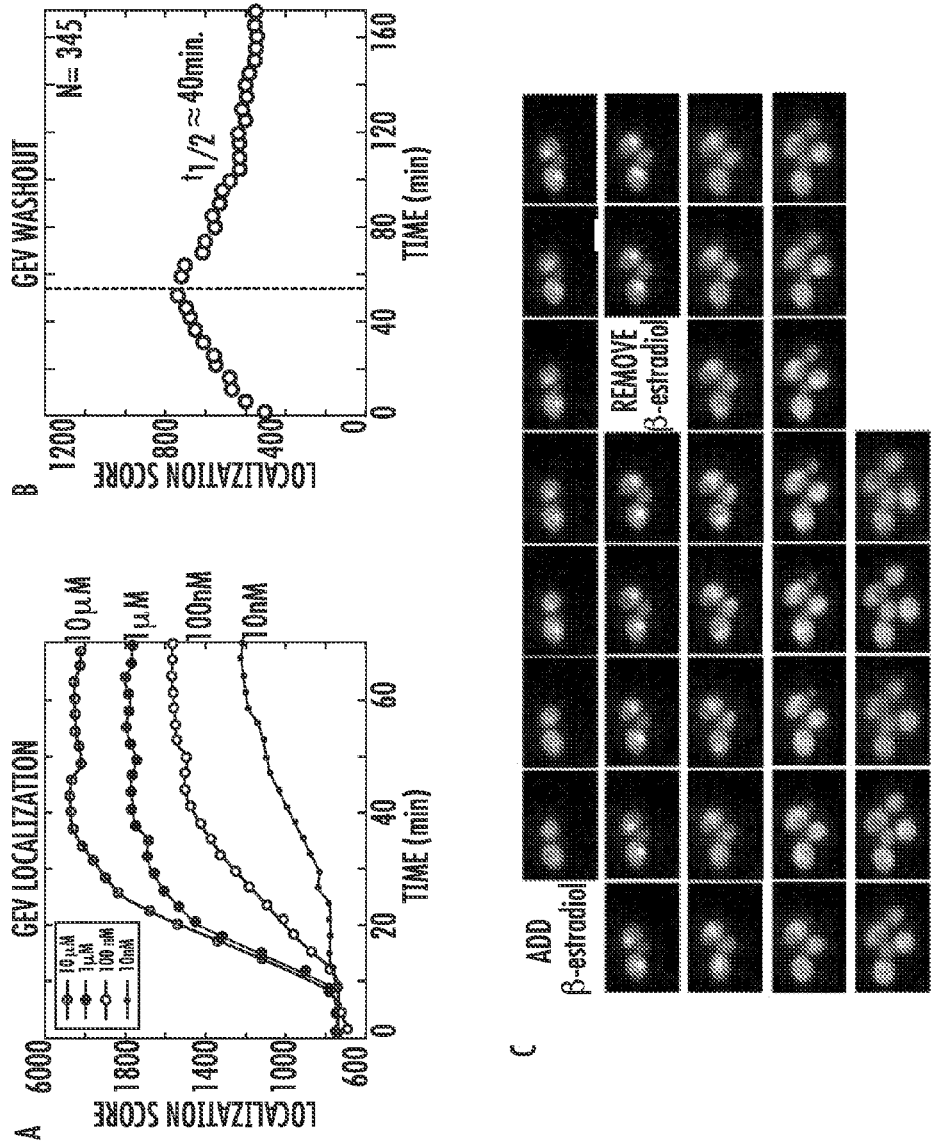
FIG. 2: Single-cell analyses of a GEV-GFP fusion protein. (A) Measuring nuclear localization of GEV-GFP in the presence of different amounts of β-estradiol in DBY11415. (B) DBY11415 was grown in the presence of 1 μM β-estradiol for 50 minutes. The input media was then switched to media lacking β-estradiol and the kinetics of de-localization were quantified. (C) Images of single cells from the washout experiment in (B). For each cell, the Localization Score is defined as the average of the top 5% of pixel intensities divided by the mean pixel intensity over the entire cell (CAI et al. 2008).

To determine the residence time of activated GEV after removal of β-estradiol, cells were grown in a flow chamber. For the first 50 minutes, medium containing 1 μM β-estradiol was flowed over the cells. Then the medium inflow was switched (FIG. 2B, black line) to a medium lacking β-estradiol, resulting in an approximately exponential reduction in nuclear fluorescence with time. This demonstrated that nuclear half-life of GEV is about 40 minutes (FIG. 2B, 2C).

Example 3

Kinetics of GEV-Mediated Gene Induction

Figure 3:
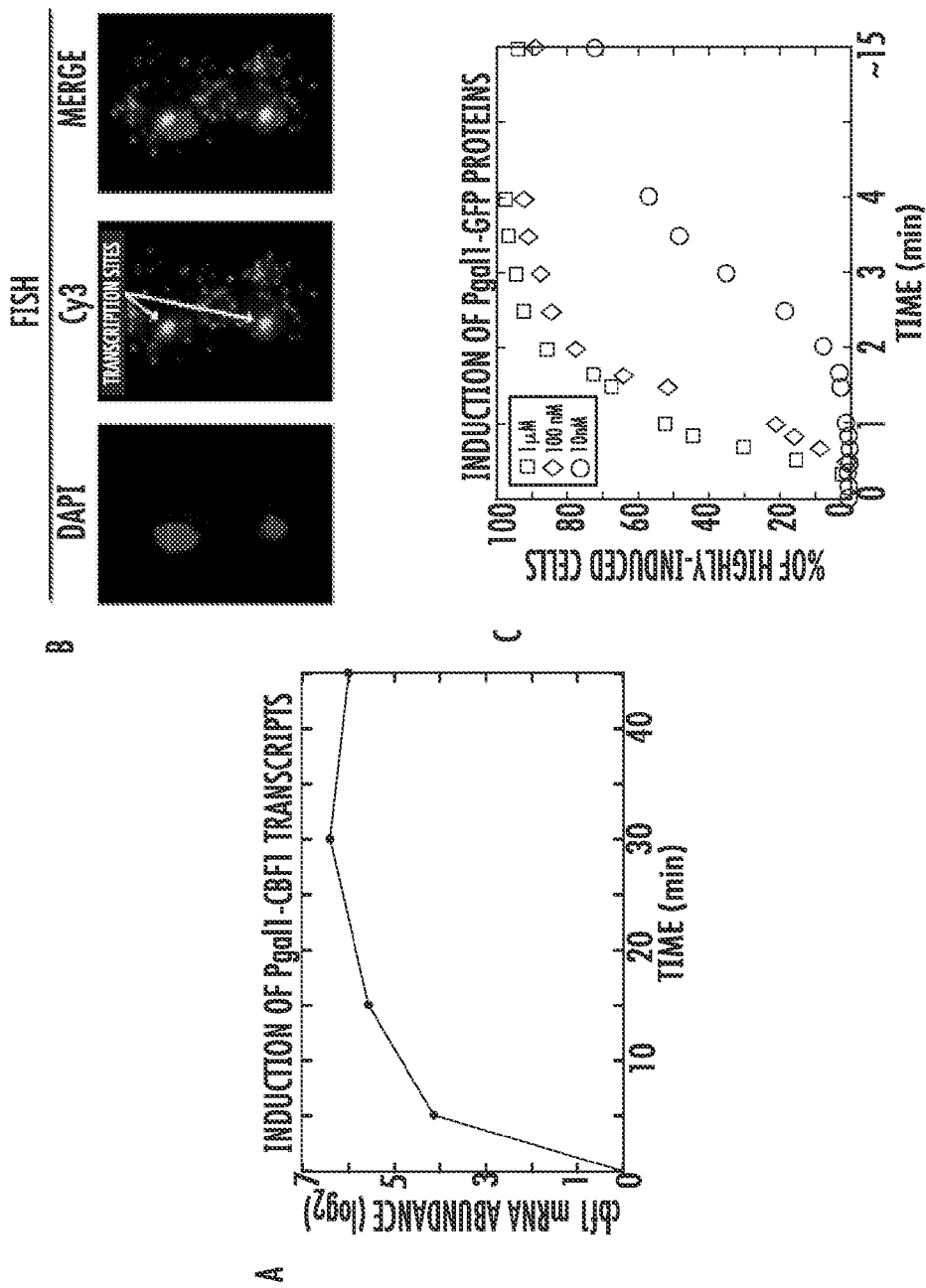
FIG. 3: The kinetics of GEV-mediated genetic switch. (A) Transcription of $P_{GAL1}$-CBF1 induced by GEV was monitored by microarray (strain=DBY12040), with DBY12001 RNA as a reference. Values are zero-normalized. (B) Maximal image projection of CBF1 transcripts from DBY12040 8 minutes after β-estradiol addition to the media (FISH). Active transcription sites of $P_{GAL1}$-CBF1 can be seen in single cells. (C) GEV activation of a $P_{GAL1}$-GFP reporter in DBY12039.

To investigate the kinetics of target gene induction by GEV, the GAL1 promoter ($P_{GAL1}$) was inserted in front of various reporter genes. First, a strain was constructed where $P_{GAL1}$ is driving transcription of the CBF1 gene at its native chromosomal locus. Upon GEV activation, the level of CBF1 transcript reaches ~70% of its maximal value by 5 minutes following addition of β-estradiol (FIG. 3A). Using Fluorescence in situ Hybridization (FISH), both the cytoplasmic transcripts and nuclear transcription sites of CBF1 were observable, as shown in the image from FIG. 3B, which was taken 8 minutes following β-estradiol to the culture. A $P_{GAL1}$-GFP reporter was used to find the point at which GEV becomes saturated by inducer. The percentage of induced cells is determined (see Materials and Methods) over time and the results indicate that GEV is saturated between 100 nM and 1 μM β-estradiol, as the induction kinetics are very similar between these two concentrations (FIG. 3C).

Example 4

GEV-Mediated Gene Induction Shows a Graded Response

Figure 4:
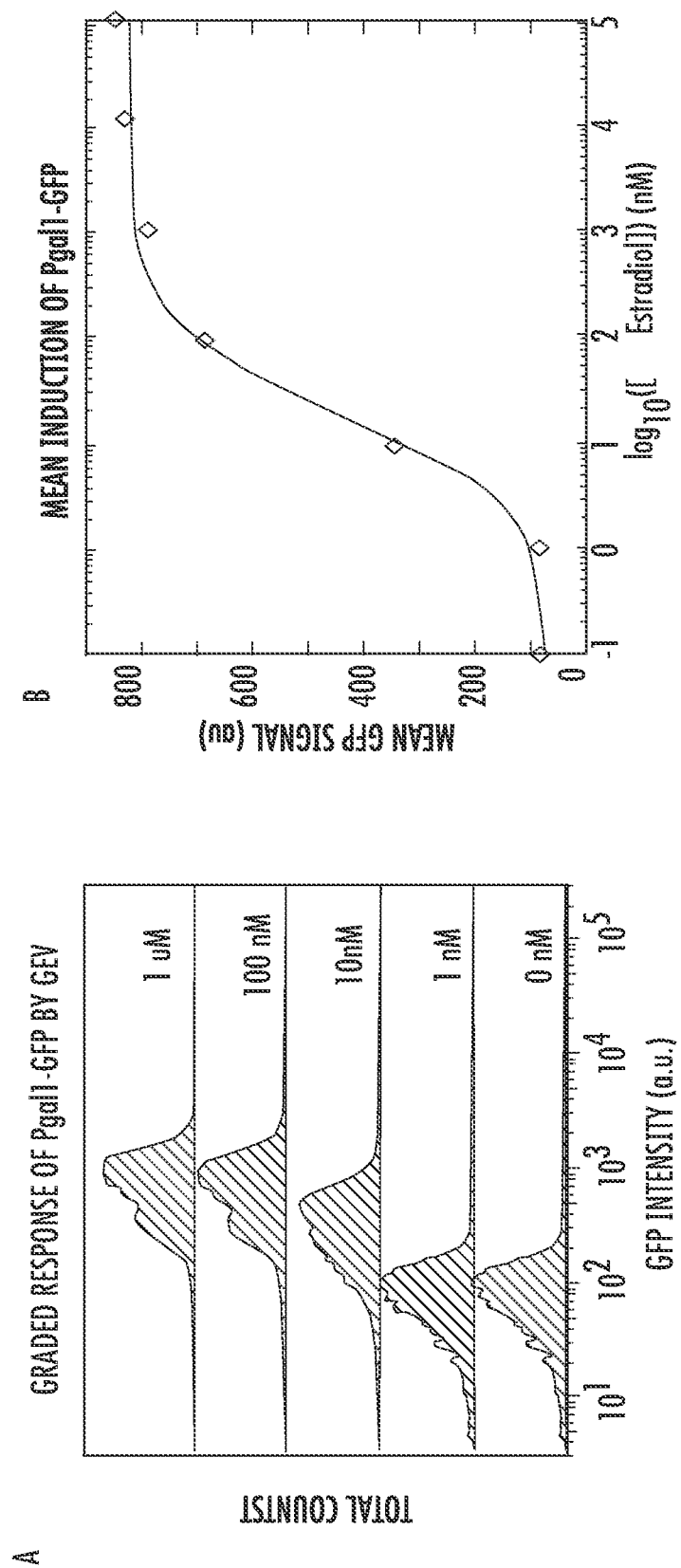
FIG. 4: GEV activity shows a graded response following β-estradiol addition. (A) Histograms of flow cytometry data at different doses of β-estradiol. Mid-log grown cells were grown to mid-log phase and incubated with the indicated amount of β-estradiol for 12 hours. (B) The mean GFP intensity from histograms in (A) as a function of β-estradiol dose. The strain used in this experiment is DBY12039.

The generally accepted model for the mechanism of nuclear receptors predicts that at sub-saturating concentrations of inducer, one should observe a steady-state response that is graded, as opposed to switch-like (Takahashi and Pryciak, 2008). Data from flow cytometry support this model for GEV induction of the galactose promoter-driven GFP construct. At concentrations below 1 nM β-estradiol, the average intensity is near the background after twelve hours of incubation (FIG. 4A). At 10 nM the average intensity is increased but well below what is achieved at higher inducer concentrations (FIG. 4B); the significant point is that all the cells exposed to 10 nM β-estradiol exhibit significant fluorescence, as shown by the shift of the entire distribution to the right (FIG. 4A). At 100 nM, the average intensity induction is near maximum, and the distribution of cells resembles closely that found for higher, completely saturating concentrations of inducer.

Example 5

The Connection Between GEV Expression and Cell Growth

Figure 5:
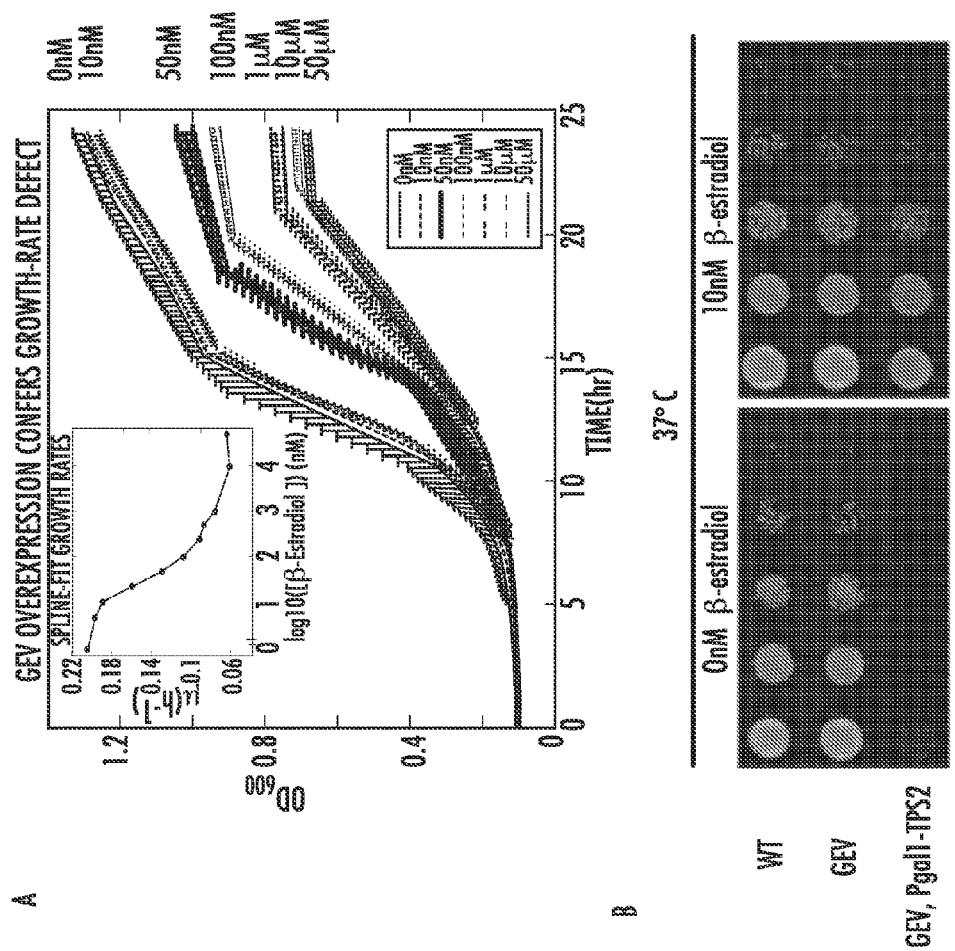
FIG. 5: GEV is a constitutive inducer at 10 nM β-estradiol without a growth defect. (A) DBY12021 grown in YPD liquid in the presence of β-estradiol. OD was monitored over time and growth rates were spline-fit (inset). Error bars represent plus/minus one standard deviation of three replicates. (B) The heat sensitivity of tps2Δ is repaired by GEV-mediated induction of TPS2. (WT=DBY12001; GEV=DBY12021; GEV+$P_{GAL1}$-TPS2=DBY12086).

The ACT1 promoter is known to be a relatively strong promoter, thus full induction in the experimental system should result in overexpression of most GEV targets. Despite the deletion of the GAL1 locus, the predicted strong GEV activation achieved at high concentrations of β-estradiol resulted in a slowing of growth (FIG. 5A). This is not due to β-estradiol toxicity because the slow growth does not occur in a strain lacking the GEV system. This could well be due to "squelching" (GILL and PTASHNE 1988), whereby strong transcriptional activators repress off-target genes through titration of the RNA polymerase machinery, and thus reduce the cell's capacity for growth. At lower concentrations of β-estradiol (10 nM), the GEV-containing cells no longer show the growth defect (FIG. 5A), but are able to induce the $P_{GAL1}$-GFP reporter essentially in all the cells nonetheless (FIG. 4A).

In order to determine whether physiologically significant expression is induced at intermediate (10 nM) levels of induction, where no growth consequence is observed, an experiment was undertaken in which a lethal defect might be complemented in a GEV-dependent manner. TPS2 encodes an enzyme that converts trehalose-6-phosphate to trehalose. Deletion of TPS2 causes a heat-sensitive growth phenotype, likely due to the build-up of trehalose-6-phosphate (DEVIRGILIO et al. 1993). By placing TPS2 downstream of $P_{GAL1}$, cells become heat sensitive in the absence of β-estradiol (FIG. 5B). Growth is restored to wild type levels in the presence of 10 nM β-estradiol, and the resulting growth is indistinguishable from wild type (FIG. 5B). This result suggests that maximal induction is not likely to be necessary in order to achieve physiological levels, and therefore that intermediate levels of inducer suffice to avoid the growth-inhibiting side effects.

Example 6

GEV Induction in Chemostats:

Since yeast are extremely sensitive to slight changes in the extracellular environment, the ideal growth setting for induction experiments is in the chemostat. Briefly, a chemostat works by flowing fresh media into a growth vessel, and culture medium is diluted from the vessel at a rate determined by the experimenter. This experimental setup allows for the growth of a culture of cells containing the GEV machinery and $P_{GAL1}$ fused to any gene of interest to steady state. In the absence of β-estradiol, the cells are effectively deletion mutants of the gene of interest. Adding β-estradiol to such cultures, strongly induces the gene of interest so that the physiological consequences can be followed. For the particular case of genes encoding transcription factors, the consequence to be followed is the genome-wide transcriptional response of the cells. The goal is to infer the immediate targets of the factors and their relative strengths of response. For those that respond most quickly, the further inference of causation is strengthened.

Example 7

Figure 6:
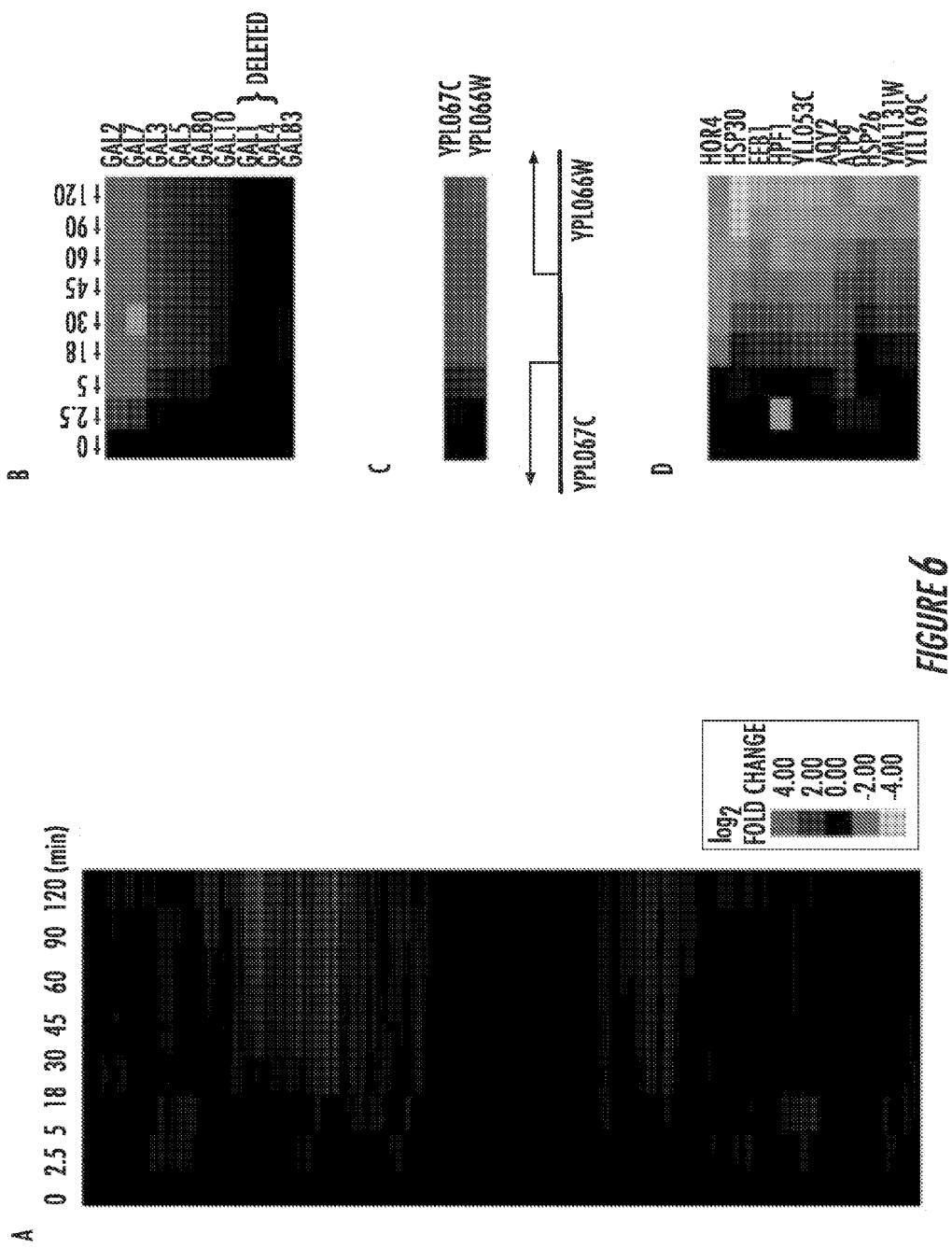
FIG. 6: (A) Hierarchical clustering of gene expression of DBY12021 grown to steady-state in a phosphate-limited chemostat with a doubling time of 4.3 hours, and at t=0, pulsed with 1 μM β-estradiol. (B) Clustergram of the GAL genes from the experiment in (A).
Figure 17:
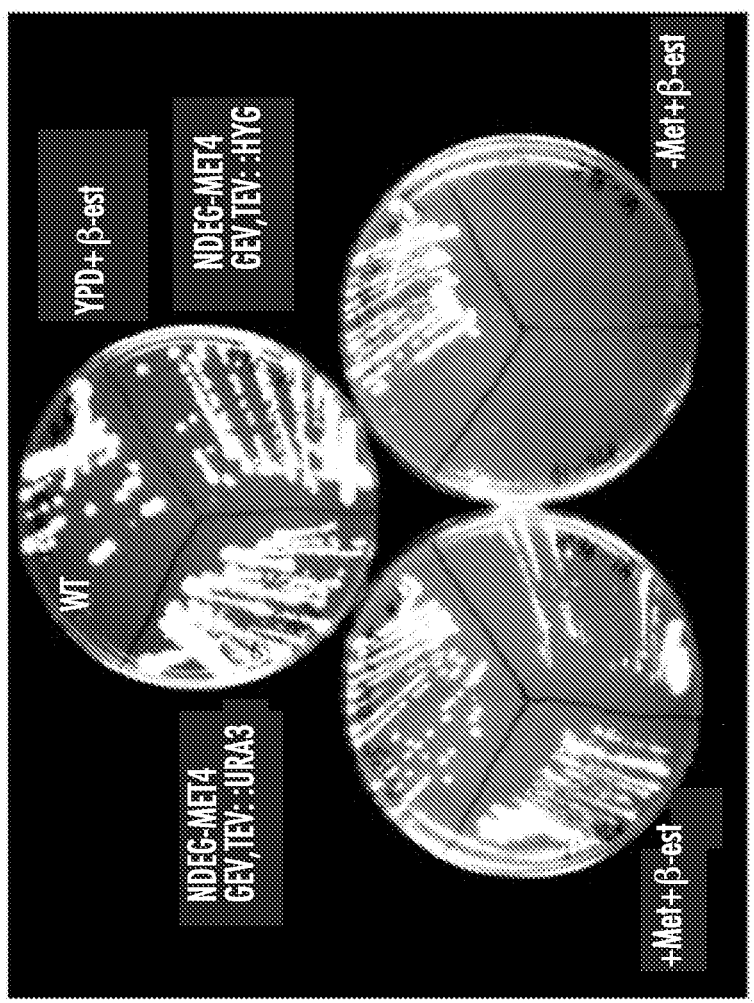
FIG. 17: Demonstration of the met phenotype of NDeg-MET4. In the presence of β-estradiol, NDeg-MET4 is met-. gal1::TEV::URA3 is equally as effective as gal1::TEV::HphMX.

GEV Induction in a Steady-State Culture is Nearly Gratuitous:

For this approach to be effective, GEV needs to be nearly gratuitous, meaning that it doesn't have a large effect on the transcriptional landscape of the cell. We can define a large effect as one that results in strong increases/decreases in many genes such that it becomes difficult to separate out changes due to overexpressing the target gene and background. By growing a strain (DBY12021) that contains GEV in a chemostat with the appropriate GAL machinery removed, we find that GEV is nearly gratuitous (FIG. 6A). In DBY12021, the GAL1 gene is deleted, as is the GAL10 promoter. Two hours following saturating (1 µM) β-estradiol addition, 105 genes decrease 2-fold (Table 3, below) and 94 genes increase 2-fold (Table 2) (FIG. 17). This accounts for about 3% of all S. cerevisiae genes. Using GO-term finder to find enriched processes within these groups, repressed genes are most enriched for glucose catabolic processes (corrected p-value=$8.49 \times 10^{-9}$) and activated genes are most enriched for oxidation-reduction processes (corrected p-value=$1.73 \times 10^{-7}$).

GEV induction results in strong activation of GAL2 and GAL7 and moderate induction of GAL3, GAL5, and GAL80 (FIG. 6B). Surprisingly, despite the removal of the GAL10 promoter by loxP in DBY12021, we observe slight induction of GAL10 over the course of the experiment.

We found two genes (YPL067C and YPL066W) that are divergently transcribed in response to GEV induction (FIG. 6C). These genes are reminiscent of GAL1 and GAL10, which are divergently transcribed in response to GAL4 activation. YPL066W and YPL067C are separated by a 385-nucleotide region. This region contains a single $UAS_{GAL}$ sequence. This sequence is conserved upstream of the YPL066W and YPL067C orthologs in S. mikatae and S. paradoxus. Despite the conservation of the GAL4 binding site, these genes have no known role in galactose metabolism and are of unknown function.

The ten genes mostly strongly repressed at 2 hours following GEV activation are shown in FIG. 6D. We could not find any significant correlation with annotated functions these genes might hold in common.

Example 8

Using GEV Overexpression to Probe Kinetics of Transcriptional Regulatory Networks Large-scale ChIP-chip studies have defined extensive transcription factor-DNA binding maps, yielding a highly informative, though static, view of genetic regulation. Using the GEV system to induce rapid and high-level expression of a single transcription factor allows observation of the dynamics of activation or repression of each of its targets.

Figure 7:
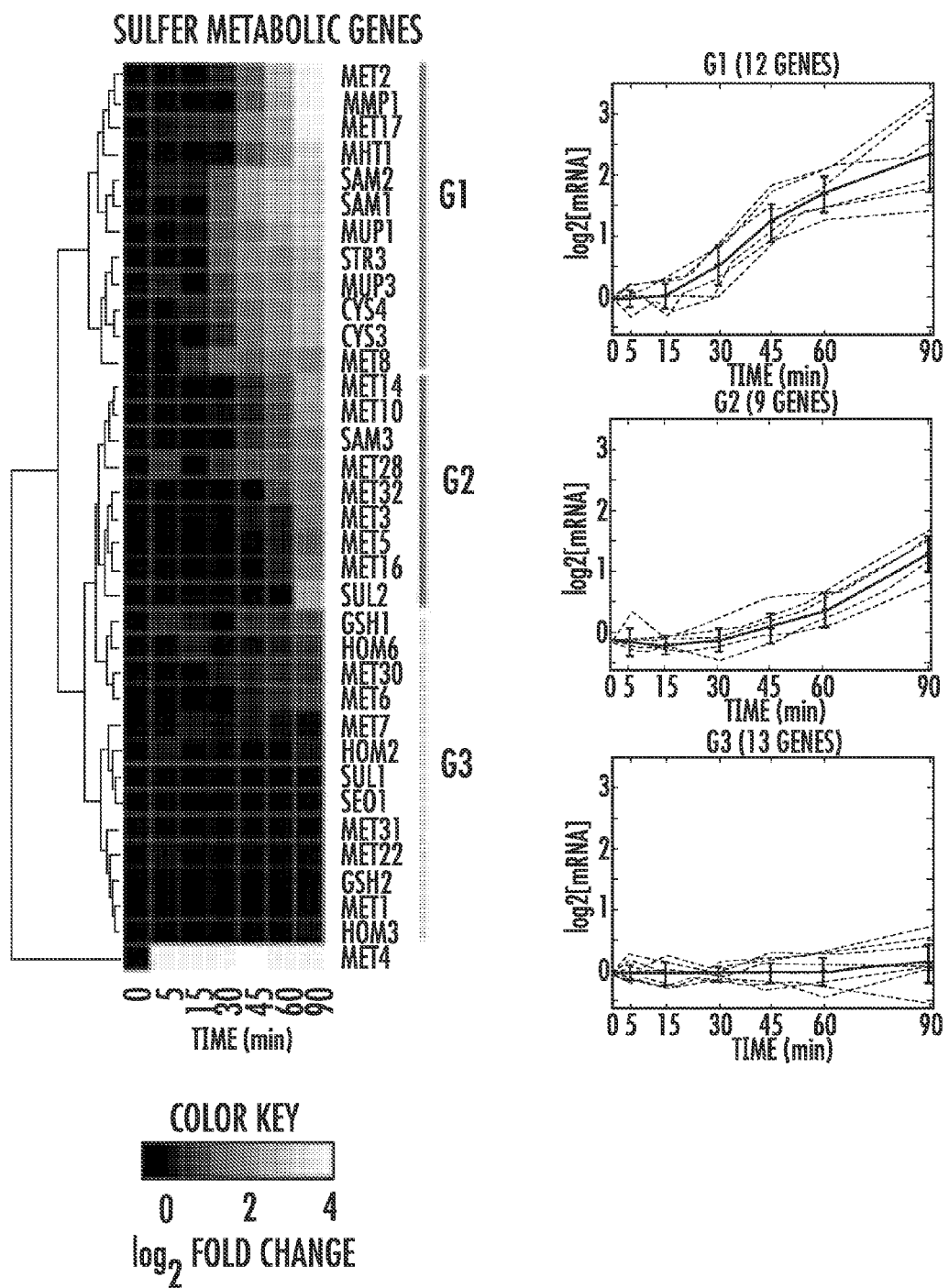
FIG. 7: Quantifying the kinetics of MET4's downstream targets. DBY12027 (GEV, Pgal-Met4) was grown to steady-state in a phosphate-limited chemostat with excess methionine (200 mg/L) with a doubling time of 4.3 hours. At t=0, cells were pulsed with 1 μM β-estradiol. (left) Hierarchical clustering of the MET4-regulated sulfur metabolic genes with three clearly identifiable categories based on kinetics. (right) The mean expression of genes in each category is plotted (thick lines connecting points) along with individual traces (gray lines). Error bars represent plus/minus 1 standard deviation of the mean.

The MET4 gene encodes a well-studied, strong transcriptional activator of the sulfur metabolic genes in S. cerevisiae and served to exemplify that the inventive system serves as a powerful tool for observing genetic regulation. A strain containing $P_{GAL1}$-MET4 was grown to steady state in a phosphate-limited chemostat containing high levels of extracellular methionine, a condition in which Met4p is supposed to be less active. By hierarchically clustering the transcriptional profile of the sulfur metabolic genes as a time series up to 90 minutes following MET4 induction, we were able to observe that the kinetics of MET4-target induction can vary from gene to gene (FIG. 7).

The targets fell into three categories based on their kinetic profiles: strongly induced (group 1), weakly induced (group 2), and uninduced (group 3). The MUP1 and MUP3 genes, which encode the high- and low-affinity methionine permeases, respectively, and SAM1 and SAM2, which encode enzymes that catalyze the synthesis of S-adenosylmethionine (AdoMet), are strongly induced group 1 genes. AdoMet is the primary source of methyl donor groups in the cell.

The MET31 and MET32 genes encode homologous zinc-finger proteins (46% identical), which aid in the recruitment of Met4p to many sulfur metabolic gene promoters. Unexpectedly, while MET32 is weakly induced (group 2), we do not detect any induction of MET31. While met31Δ and met32Δ mutant cells are able to produce their own methionine when grown on minimal medium, met31Δmet32Δ double-mutants are methionine auxotrophs. Despite the purported redundancy of these factors, we were able to observe differential regulation in response to MET4 overexpression.

Example 9

Figure 8:
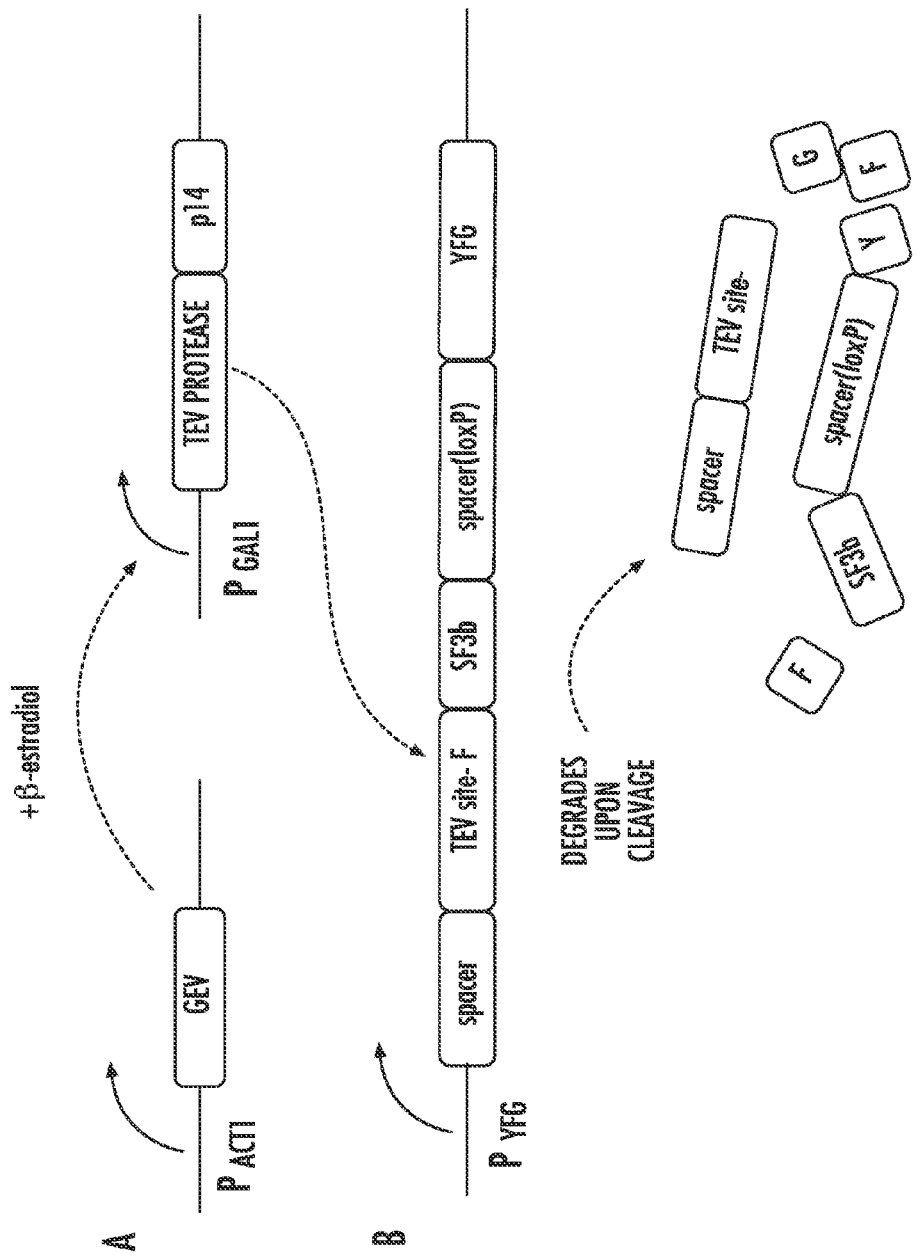
FIG. 8: (A) GEV is expressed under the regulation of the constitutive ACT1 promoter. Treatment with β-estradiol induces nuclear entry and induction of $P_{GAL1}$-driven TEV. (B) The target gene of interest (YFG) is regulated by its native promoter. TEV protease binding to its cleavage site in TDeg'F modified YFG, facilitated by p14-SF3b binding, results in cleavage, exposing the destabilizing amino acid phenylalanine at the amino terminus Proteasome-mediated digestion of YFG is the result of N-end rule degradation pathway.
Figure 9:
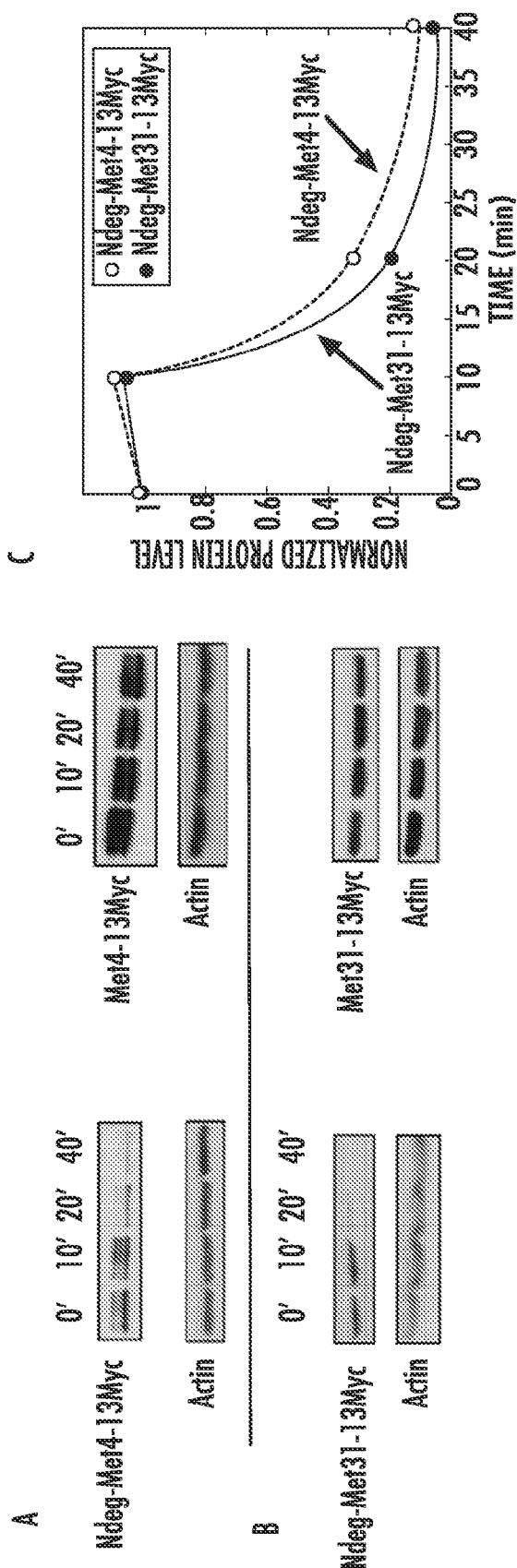
FIG. 9: (A) Western blot of DBY12055 (NDeg-Met4p-13Myc) and DBY11440 (Met4p-13Myc) prior to (0') and following (10', 20', and 40') 1 μM β-estradiol to the culture. (B) Western blot of DBY12234 (NDeg-Met31p-13Myc) and DBY12235 (Met31p-13Myc) prior to (0') and following (10', 20', and 40') 1 μM β-estradiol to the culture. (C) Normalized protein levels from experiments in 9A and 9B with DBY12055 and DBY12199. Protein levels were quantified in ImageJ and then fit to a power-law for the 10', 20', and 40' time points.
Figure 10:
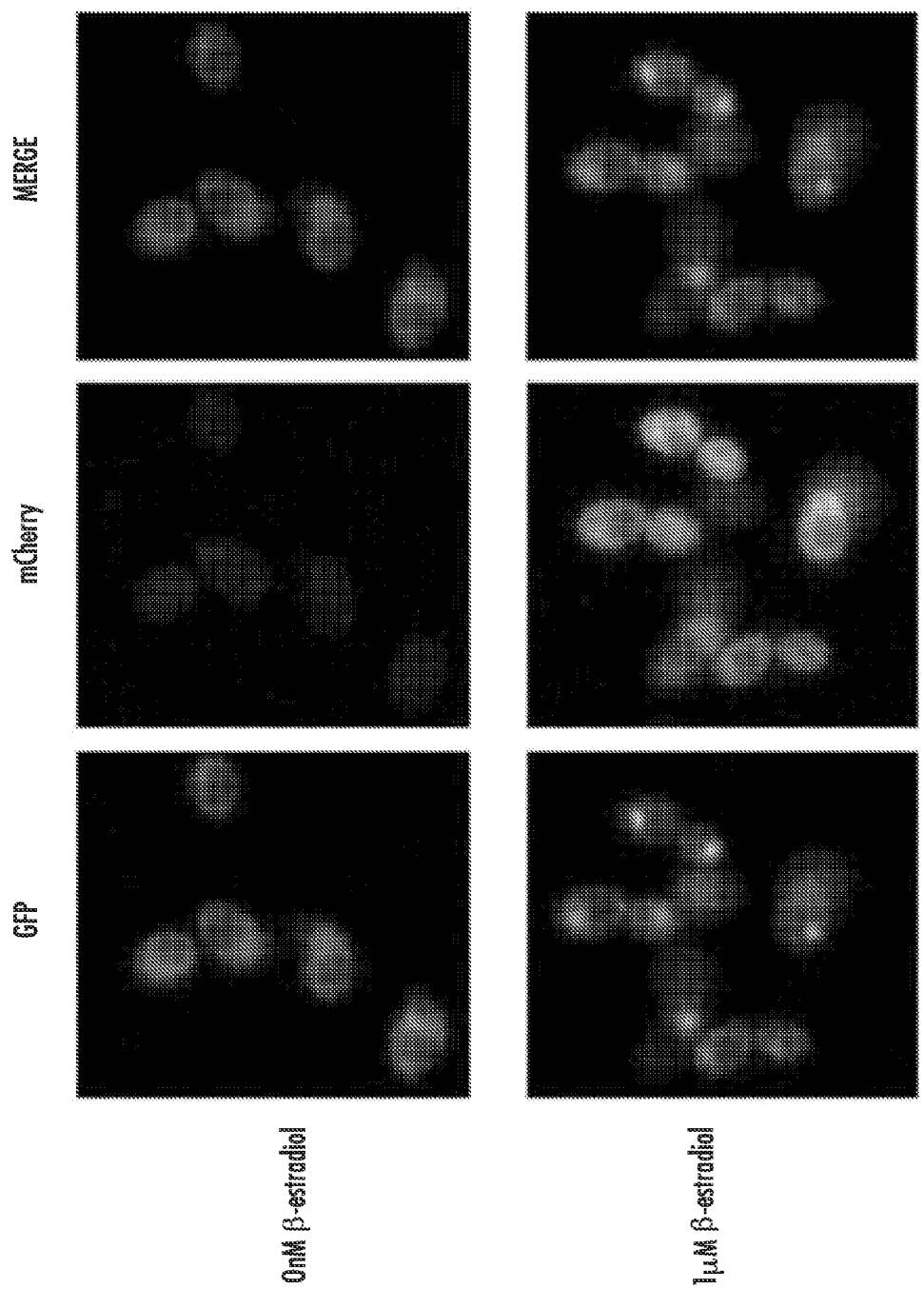
FIG. 10: The GEV-GFP fusion protein is functional. Cells containing GEV-GFP and a GAL1-mCherry fusion are grown in the absence (top) or presence (bottom) of β-estradiol.

GEV-Mediated Induction of TEV Results in Rapid Degradation of N-Degron-Tagged Proteins:

MET4 and MET31 genes were chosen for use in a proof of principle experiment to exemplify the protein depletion method (FIG. 8). We constructed Ndeg-modified MET4 and MET31 alleles in separate strains containing GEV and $P_{GAL1}$-TEV (see Materials and Methods). Cells were grown in rich medium (YPD) and treated with 1 µMβ-estradiol at ~$2 \times 10^7$ cells/mL. Western blots were performed on proteins extracted at several time points after induction (FIG. 9). Treatment of cultures with 1 µM β-estradiol had no effect on levels of Met4p-13Myc or Met31p-13Myc lacking NDeg (FIG. 9A, 9B). However, 1 µM β-estradiol treatment of NDeg-MET4 or NDeg-MET31 cells showed rapid reduction of the NDeg-tagged proteins (FIG. 9A, 9B). By performing a best fit of the data from 10, 20, and 40-minute timepoints to a power-law, we find that the half-life of NDeg-Met4p-13Myc is 16 minutes and that of NDeg-Met31p-13Myc is 13.75 minutes (FIG. 9C).

A met4 null allele has a growth defect and produces small colonies on YPD plates (Hickman et al., 2011). Therefore a diploid cell was used for construction of NDeg-MET4. Sporulation of this diploid followed by dissection of the resulting tetrads showed that the spore colonies had the same wild type size, confirming that the modified gene was functional.

Met4p is known to be ubiquitinated (Rouillon et al., 2000) and is, as a result, unstable. Three clear bands were observed in our Met4p Western blots, consistent with the presence of non-ubiquitinated Met4p in addition to heavier ubiquitinated forms (FIG. 9A). When MET4 is tagged with NDeg, both the ubiquitinated and non-modified Met4p proteins are targeted for degradation by TEV (FIG. 9A).

Finally, the phenotypic effect of β-estradiol treatment of NDeg-MET4 containing cells was assayed. As expected only cells treated with β-estradiol displayed a methionine auxotrophy (met) phenotype (FIG. 17), as Met4p is required for methionine synthesis (Masselot and Robichon-Szulmajster, 1975).

Example 10

Characterization of ZEV and 4ZEV Activity

The ZEV and 4ZEV transcriptional activators have the same hormone binding domain and activator domain as GEV, but each has a different DNA binding domain. ZEV has the DNA binding domain of transcription factor zif268 and 4ZEV has a rationally designed four zinc fingers domain.

Figure 21:
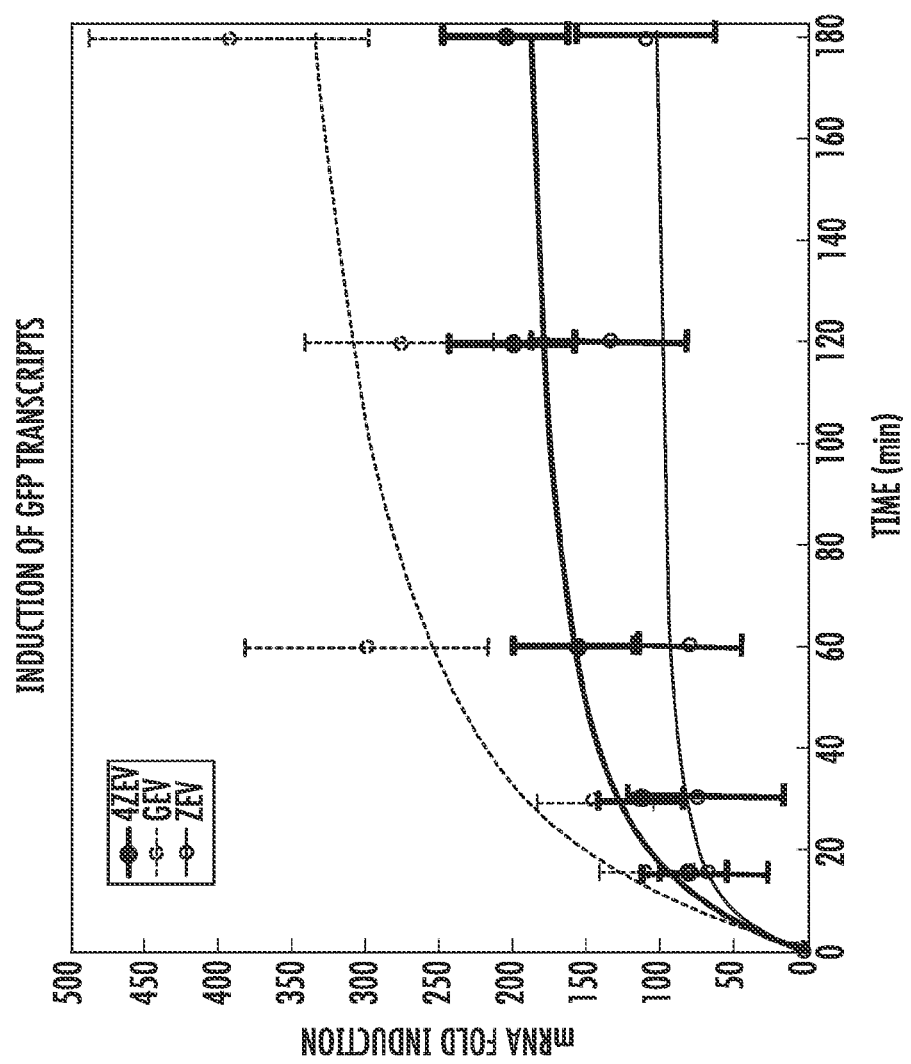
FIG. 21: Fold-induction of GFP transcripts by the three gene expression systems. Error bars represent standard error of the mean for three technical replicates.
Figure 22:
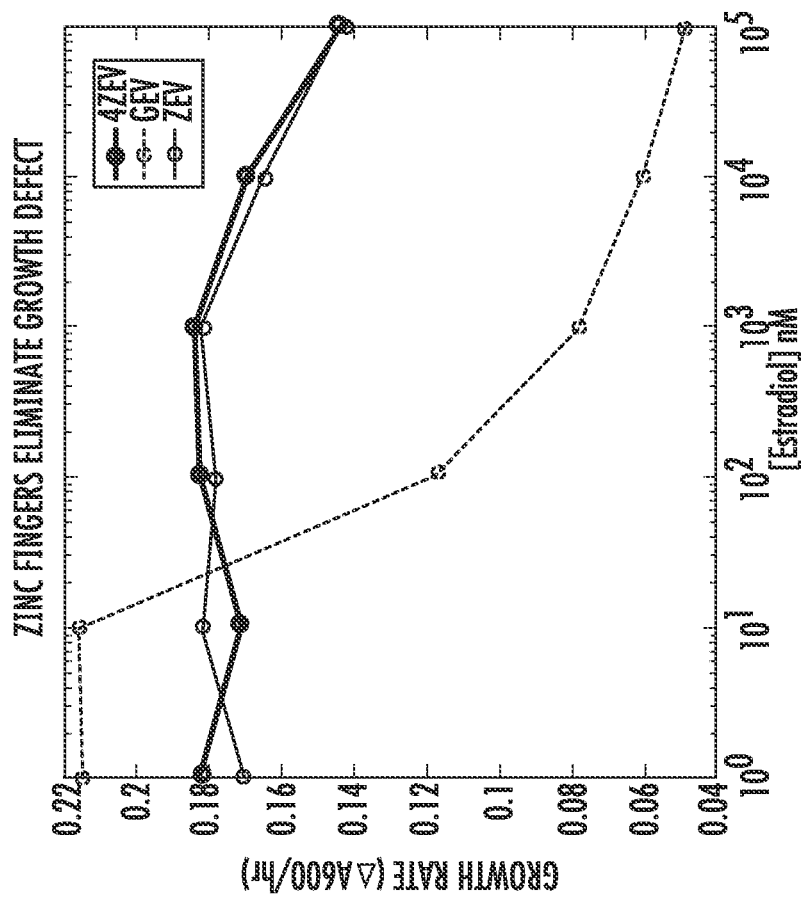
FIG. 22: Using the zinc finger DNA binding domains eliminates the growth rate associated with GEV.

The performance of these protein transcription factors are shown in FIGS. 18-22. FIG. 18 shows the reporter plasmids used for characterizing the different expression systems. By placing the binding sites between restriction sites, new binding sites can be cut-and-pasted with relative ease. Thus, input/output relationships can be easily tested for different DNA binding sequences. Importantly, each of the three systems show a graded response, FIG. 19B), and the use of non-yeast DNA binding domains allows for more production of GFP (FIG. 19A,B), presumably through a reduction in the errant transcriptional responses associated with the GEV system. Importantly, the ZEV and 4ZEV systems eliminate the expression changes associated with the GEV system (FIG. 20A,B). Nonetheless, each system strongly induces GFP (FIG. 20C), and each system induces GFP transcripts >50-fold by 15 minutes following hormone addition (FIG. 21). Finally, by reducing the background expression of these new systems, the growth defect associated with GEV is eliminated (FIG. 22). This makes the new systems ideal for a variety of applications where 1) remaining inert with respect to the cell's overall physiology and 2) reducing background expression is of importance.

Discussion

This system demonstrates that the hormone-inducible transcriptional activator is an efficient switch that induces target genes to near maximal levels within minutes following hormone addition to the culture. A single-cell visualization method was used to establish that GEV activation occurs by its rapid nuclear localization in the presence of β-estradiol. The system demonstrated that GEV overexpression results in minimal errant induction of genes in a Δgal1 background, making it ideal for overexpression studies in *S. cerevisiae*.

With the endogenous galactose utilization machinery deleted, the results indicated that such a system (a) can be nearly gratuitous, as indicated by genome-wide profiling; (b) is fast acting, requiring only several minutes to activate transcription; and (c) exhibits low translational noise.

GEV induces or represses relatively few genes in a Δgal10Δgal1Δgal4 background. A 3-hour time course of DBY12021 (leu2Δ0::pACT1-GEV-NatMX, (Pgal10-1+Gal1)::loxP, Gal4::LEU2, HAP1+) following a pulse with β-estradiol showed that GEV-mediated activation by estradiol affects relatively few genes in the genome, less than 2% of the entire genome according to measurement by K-means clustering of time course data.

Figure 11:
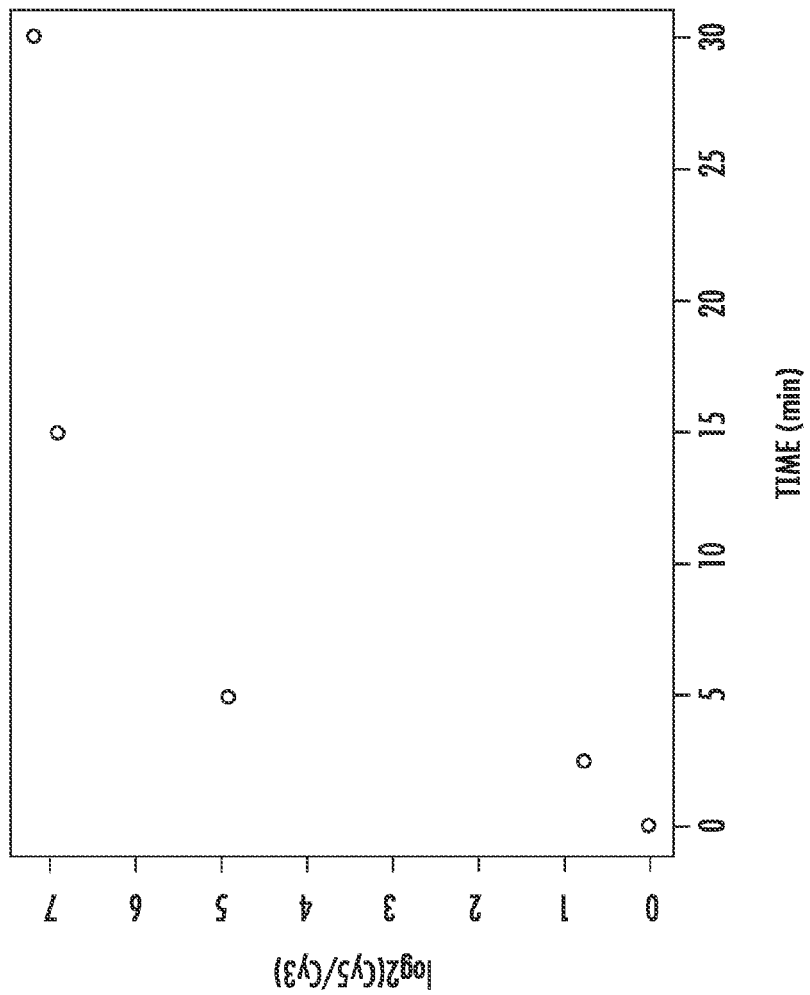
FIG. 11: GEV induction of Pgal1-MET4 transcripts. Transcription of Pgal1-MET4 induced by GEV was monitored by microarray (strain=DBY12099), with DBY12001 RNA as a reference. Values are normalized to t=0.
Figure 12:
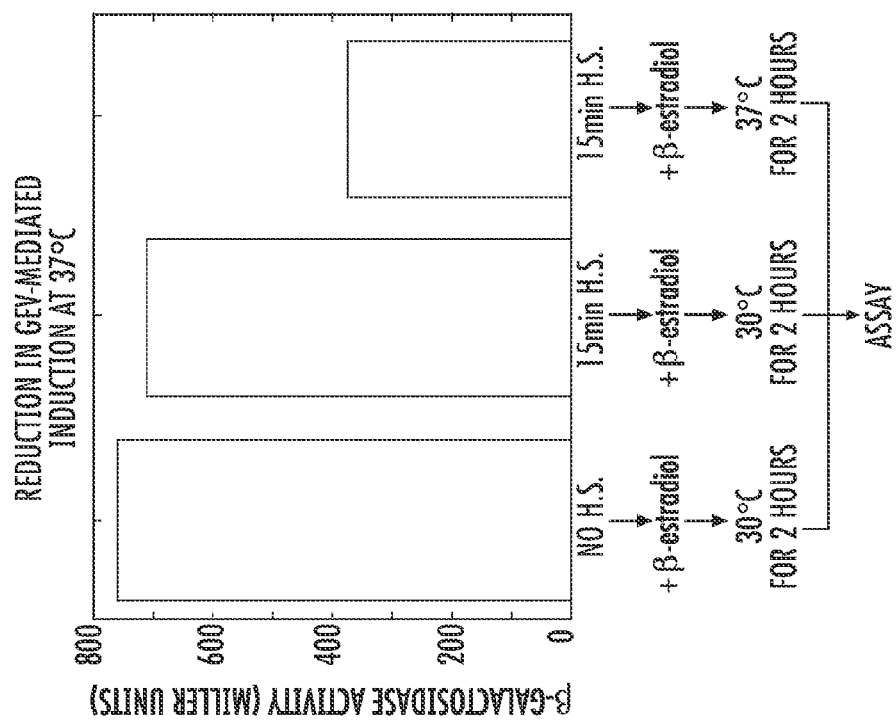
FIG. 12: GEV has reduced activity at 37° C., as measured in DBY12100+$P_{GAL1}$-lacZ reporter plasmid (pCM64-GAL1). Log-phase cells were grown at 30° C., before either being maintained at 30° C. (left) or heat shocked at 37° C. for 15 minutes (middle, right). Cells were then pulsed with 1 μM β-estradiol and transferred to either 30° C. (left, middle) or 37° C. (right). After two hours of incubation, lacZ activity was measured.
Figure 13:
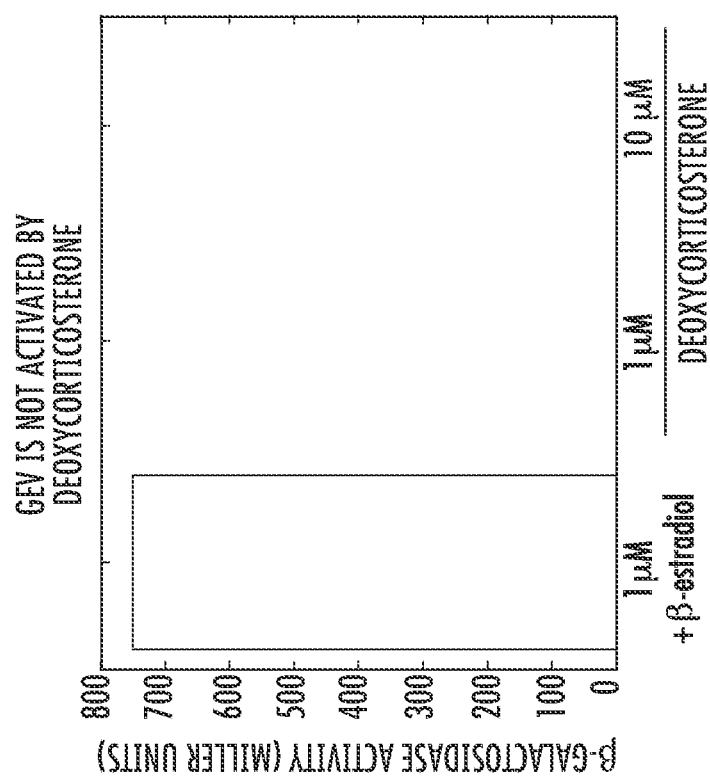
FIG. 13: GEV is not induced by the hormone deoxycorticosterone, an inducer of glucocorticoid receptors. As in FIG. 11, log-phase DBY12100+pCM64 were incubated with the indicated amount of β-estradiol or deoxycorticosterone for 2 hours and lacZ activity was then measured.

The examples show that the GEV system, configured in the manner of the invention, satisfies the requirements of an effective gratuitous induction system. It can be used to both rapidly induce a target gene in every cell in the culture while conferring minimal induction of off-target genes. GEV provides efficient induction. The range of transcription rates in *S. cerevisiae* measured in the literature ranges from 0.7-2 kb/min (MASON and STRUHL 2005; ZENKLUSEN et al. 2008), the upper bound of which has been measured from a $P_{GAL1}$-driven gene (MASON and STRUHL 2005). If a gene is 2 kb in length and is downstream of $P_{GAL1}$, as in the case of $P_{GAL1}$-MET4, generating a full transcript should take 1 minute. By 2.5 minutes, detectable amounts of $P_{GAL1}$-driven transcript were observed (FIG. 11). By 2.5 minutes, therefore, the gene has gone through several rounds of transcription. By 5 minutes, the amount of induction is near-maximal.

In the localization experiments herein, GEV-GFP is detected in the nucleus at ~6-8 min. following addition of β-estradiol to the media. If nuclear localization takes ~6-8 min., it would appear surprising that full-length transcripts are measured at 2.5 minutes following β-estradiol addition to the media. There are at least two potential explanations. First, it can be accounted for if the GEV-GFP fusion has slightly slower kinetics of nuclear localization than GEV. Second, it can be accounted for if the kinetics of GEV-GFP reflects the kinetics of GEV without the fluorescent tag, but measurement of localization is too insensitive to detect the first few GEV-GFP molecules that become localized to the nucleus and activate transcription.

Opportunities for Dynamic Studies of Regulation:

One of the most significant advantages of the system is the potential for following the consequences of the induction of a specific protein dynamically. This is clearest in the case of a transcriptional regulator like Met4p. The induction kinetics allow us to distinguish primary from secondary targets, and the cascade of consequences can be followed as time series that can shed light on the sequence of events under a variety of physiological conditions.

Through overexpression of MET4, the kinetics of induction of the sulfur metabolic genes was distinguishable (FIG. 7). The kinetics of target induction can depend strongly on the choice of nutrient limitation (i.e., phosphate versus methionine limitation). ChIP-chip studies can show the presence or absence of transcription factor-DNA interactions. They fail, however, to capture the strength and kinetics of induction of a particular gene in response to a single factor, something that is readily measurable via GEV-mediated overexpression of particular transcription factors.

By finding motifs in the promoters of genes that rapidly change expression in response to overexpression of a particular transcription factor, we can potentially generate position weight matrices (PWMs) for factors with unknown DNA binding motifs. Another potential application is to refine known PWMs of better-studied factors by complementing previous in vitro and context-specific ChIP-chip data with in vivo measurements that look for the presence of direct regulation through GEV-mediated overexpression.

Upon removing β-estradiol from the media, GEV-GFP begins to delocalize within minutes (FIG. 2B). In the presence of β-estradiol, cytoplasmic GEV binds β-estradiol and enters the nucleus at a rate $k_{in}$. Nucleus-localized GEV is either bound to or unbound from DNA. Unbound GEV diffuses throughout the nucleus and exits the nucleus at a rate $k_{out}$. Since $k_{in}$ approaches 0 in the absence of β-estradiol, we can immediately measure unbound GEV leaving the nucleus at rate $k_{out}$. However, the true rate of nuclear delocalization of GEV includes the unbinding of GEV from DNA, which can be much slower.

Given that the half-life of GEV nuclear localization is ~40 minutes and that protein half-lives can be as large as days, removing β-estradiol from the media is not an effective way to quickly deplete the levels of a target protein. Similarly, methods that rely on blocking transcription upon addition of inducer to cells are not effective for rapidly depleting target proteins. These facts were the motivation to prepare a construct to drive the expression of TEV by GEV, which allows for rapidly turning off target proteins containing an N-degron sequence. This sequence can readily be added to genes via homologous recombination. Therefore, we now have developed a method for rapidly shutting off the levels of single genes expressed from their native promoters. Upon β-estradiol addition and subsequent depletion of the target gene by TEV, one can study the cell's transient physiological response (such as the transcriptional profile) to losing both essential and non-essential genes. These types of studies assist to rigorously define the transcriptional regulatory network of essential genes in S. cerevisiae.

Various modifications and variations of the invention in addition to those shown and described herein will be apparent to those skilled in the art without departing from the scope and spirit of the invention and fall within the scope of the appended claims. Although the invention has been described in connection with specific preferred embodiments, it should be understood that the invention as claimed should not be unduly limited to such specific embodiments. All publications and patents mentioned in the above specification are incorporated in their entirety by reference.

TABLE 1

Strain list.
All strains are s288c. HAP1+ indicates a repaired HAP1 allele (Hickman and Winston, 2007) and hap1− indicates the partial loss-of-function s288c allele (Gaisne et al., 1999; Hickman and Winston, 2007).

| Strain | Genotype | Source |
| --- | --- | --- |
| DBY11389 | Mata, ura3Δ0 | This Study |
| DBY11408 | MATα, his3Δ1 leu2Δ0 lys2Δ0 ura3Δ0 gal10::KanMX | Deletion Collection |
| DBY11415 | MATa/MATα, ($P_{GAL10}$ + gal1)::loxP/GAL1, leu2Δ0::$P_{ACT1}$-GEV-GFP-KanMX/LEU2, gal4Δ::LEU2/GAL4, HTB2-mCherry-CaUra3, his-/HIS, leu-/LEU, hap1−/HAP1+ | This Study |
| DBY12020 | MATa, ($P_{GAL10}$ + gal1)::loxP, leu2Δ0::$P_{ACT1}$-GEV-NatMX, gal4Δ::LEU2, HAP1+ | This Study |
| DBY12021 | MATα, ($P_{GAL10}$ + gal1)::loxP, leu2Δ0::$P_{ACT1}$-GEV-NatMX, gal4Δ::LEU2, HAP1+ | This Study |
| DBY12027 | MATα, ($P_{GAL10}$ + gal1)::loxP, leu2Δ0::$P_{ACT1}$-GEV-NatMX, gal4Δ::LEU2, KanMX-Pgal1-MET4, HAP1+ | This Study |
| DBY12039 | MATα, ($P_{GAL10}$ + gal1)::loxP, leu2Δ0::$P_{ACT1}$-GEV-NatMX, gal4Δ::LEU2, ybr032wΔ::$P_{GAL1}$-GFP-NatMX, HAP1+ | This Study |
| DBY12040 | MATα, ($P_{GAL10}$ + gal1)::loxP, leu2Δ0::$P_{ACT1}$-GEV-NatMX, gal4Δ::LEU2, KanMX-$P_{GAL1}$-CBF1, HAP1+ | This Study |
| DBY12055 | Mata, NDeg-MET4-13Myc-KanMX, gal4::LEU2, gal1::TEV-HphMX, leu2Δ0::$P_{ACT1}$-GEV-NatMX, HAP1+ | This Study |
| DBY12086 | MATα, ($P_{GAL10}$ + gal1)::loxP, leu2Δ0::$P_{ACT1}$-GEV-NatMX, gal4Δ::LEU2, KanMX-$P_{GAL1}$-TPS2, HAP1+ | This Study |

TABLE 1-continued

Strain list.
All strains are s288c. HAP1+ indicates a repaired HAP1 allele
(Hickman and Winston, 2007) and hap1− indicates the partial
loss-of-function s288c allele (Gaisne et al., 1999; Hickman and Winston, 2007).

| Strain | Genotype | Source |
|---|---|---|
| DBY12099 | MATα, (P$_{GAL10}$ + gal1)::loxP, leu2Δ0::P$_{ACT1}$-GEV-NatMX, gal4Δ::LEU2, KanMX-Pgal1-MET4, met6Δ::HphMX4 HAP1+ | This Study |
| DBY12100 | MATα, (P$_{GAL10}$ + gal1)::loxP, leu2Δ0::P$_{ACT1}$-GEV-NatMX, gal4Δ::LEU2, ura3Δ::HphMX4, HAP1+ | This Study |
| DBY12132 | MATα, gal1::TEV::URA3, ura3Δ0, leu2Δ0::P$_{ACT1}$-GEV-NatMX, gal4::LEU2, HAP1+ | This Study |
| DBY12168 | MATa/MATα, Δgal4::LEU2/GAL4, (P$_{GAL10}$ + gal1)::loxP/GAL1-mCherry-NatMX, leu2Δ0::P$_{ACT1}$-GEV-GFP-KanMX/LEU2, HAP1+/HAP1+ | This Study |
| DBY11440 | MATa/MATα, MET4-13Myc-KanMX/MET4, ura3Δ0/URA3, gal1::TEV::URA3/GAL1, gal4::LEU2/GAL4, leu2Δ0::P$_{ACT1}$-GEV-KanMX/LEU2, hap1−/HAP1+ | This Study |
| DBY12032 | MATa, leu2Δ0 | This Study |
| DBY12194 | MATα, NDeg-MET31, gal1::TEV-URA3, fcy1::CreEDB78 | This Study |
| DBY12197 | MATa, MET31-13Myc-KanMX, can1::P$_{ACT1}$-GEV, lys2, gal1::TEV-URA3 | This Study |
| DBY12199 | MATa, NDeg-MET31-13Myc-KanMX, gal1::TEV-URA3, fcy1::CreEDB78 | This Study |
| DBY12200 | MATα, gal1::TEV-URA3, can1::P$_{ACT1}$-GEV, gal4::LEU2 | This Study |
| DBY12234 | DBY12199 × DBY12200 | This Study |
| DBY12235 | DBY12197 × DBY12194 | This Study |
| DBY11378 | MATa, his3delta1, ura3delta0, ade2delta::hisG, lys2delta0, met15delta::LYS2, distal ChrIVR-MET15, RAD52-eGFP-KANMX, leu2delta0::pACT1-GEV-NAT | Dan Gottschling UCC1909 |
| DBY11376 | MATa, his3delta1, leu2delta0, ura3delta0, ade2delta::hisG, lys2delta0, met15delta::ADE2, distal-chrIV::MET15, gal4:LEU2, pRPT1-GEV-Nat | Dan Gottschling UCC1864 |

TABLE 2

CBF1 FISH probes
The thymidines surrounded by asterisks are amino-allyl-Cy3 dye labeled.

| Probe ID | Probe Sequence | SEQ ID NO: |
|---|---|---|
| cbf1-15 | *T*CT CTT TGC TTT T*T*C CTG GCC TCG CTG *T*AG TTC TGC TCC *T*CG TTA TAG CCT C*T*T | 15 |
| cbf1-31 | *T*TC GCG TTC GTT *T*GA TTA GAT GTG *T*GG GCA TCA GAA C*T*A TCT TCC TGG CCC *T*GG | 16 |
| cbf1-48 | *T*TC TGG CCC ACG A*T*C GTG TTC TGC CAA *T*GG TAT GAG CAT G*T*C GTT TTT AGA T*T*G | 17 |
| cbf1-57 | *T*TA CTT GAT TCT C*T*C ACG GGC AGG AGG *T*CG CTT AAA ACG T*T*G ATT GCA GTG T*T*G | 18 |
| cbf1-68 | *T*CC CAG TTC TTC C*T*G CAG TTT CTC A*T*T TGC ACT GGC TAA *T*TG CGA TGC GTT T*T*G | 19 |

TABLE 3

Primers used in this study.

| Primer ID | Primer Sequence | SEQ ID NO: |
|---|---|---|
| GEVGFP-F | GATGTTTACCGATGCCCTTGGAATTGACGAGTACGGTG GGggtgacggtgctggttta | 20 |
| GEVGFP-R | TTGACCTCTAATCATGCGGCCGCTCTAGAACTAGTG GATCtcgatgaattcgagctcg | 21 |

TABLE 3 -continued

Primers used in this study.

| Primer ID | Primer Sequence | SEQ ID NO: |
|---|---|---|
| HTB2-F | tactagggctgttaccaaatactcctcctctactcaagccGGTGACGGTGCTGGTTTA | 22 |
| HTB2-R | aaaagaaaacatgactaaatcacaataccta gtgagtgacTCGATGAATTCGAGCTCG | 23 |
| MET4-Pgal1-F | TGCTGTATGAGTCGCCTTCGTGGGACTGCTCCTGCTTCATTATAGTTTTTTCTCCTTGACGTTAAAG | 24 |
| MET4-Pgal1-R | TCTCGTCAATAAAGCGCACTTCTGATAAGCACTTTTATTCGCAATTAAGAACTAAAAGATATAGAGTGC | 25 |
| CBF1-Pgal1-F | CCTCAGTAGAAAGCTTATTATTATTTGCCAGAGAGTTCATTATAGTTTTTTCTCCTTGACGTTAAAG | 26 |
| CBF1-Pgal1-R | AGTGCTTAAAATATAATACGGTTTTCTACACTTTTATTAAGCAATTAAGAACTAAAAGATATAGAGTGC | 27 |
| TPS2-Pgal1-F | AAACCAAAATAACACTGCCTGTCACTATTTCTGTGCCGAAGCAATTAAGAACTAAAAGAT | 28 |
| TPS2-Pgal1-R | TCTCTTCTTTGGAGAATTGTCTTGGGCAGTGGTGGTCATTATAGTTTTTTCTCCTTGACG | 29 |
| MET4-Tipi-F | AAAGCGCACTTCTGATAAGCACTTTTATTCCTTTTTTTCCACTGTGAACGATGTCTATTACTTCTTTGTACAAG | 30 |
| MET4-Tipi-R | CCGTGCTGTATGAGTCGCCTTCGTGGGACTGCTCCTGCTTCATTAATAACTTCGTATAGCATAC | 31 |
| MET4-Myc-F | AAAAAGCTGAAAGCTTAAAGAAGCAAATTTTTGAGAAGGTTCAGAAAGAACGGATCCCCGGGTTAATTAA | 32 |
| MET4-Myc-R | ATGCACGTATATATATATATATATATATAATTAAACTGTATAGTCTGTTATTGAATTCGAGCTCGTTTAAAC | 33 |
| MET31-Tipi-F | GTTGGGCTCAATATACACAGTCGATAGTCTATATGTGCATATGTCTATTACTTCTTTGTACAAG | 34 |
| MET31-Tipi-R | GAGAAATATTTCATCTACATTCATGTCTTGCGCCAGTTTCATTAATAACTTCGTATAGCATAC | 35 |
| overlap tipi to ycplac F | TAACAATTTCACACAGGAAACAGCTATGACCATGATTACGTCTATTACTTCTTTGTAC | 36 |
| overlap tipi to ycplac R | CAGGGTTTTCCCAGTCACGACGTTGTAAAACGACGGCCAGCATCGATGAATTCTCTGTCGTCC | 37 |
| N-deg F + lox F | GCTGGTTATGTTCCTATTCGAACTCCAGCTCATATGGATATAACTTCGTATAATGTATGC | 38 |
| N-deg R lox R | CGGCCGCATAGGCCACTAGTGGATCTGATATCATCGATAATAACTTCGTATAGCATAC | 39 |
| ATG plus tipi start F fuse | ATGTCTATTACTTCTTTGTACAAG | 40 |
| lox rev fuse | CATTAATAACTTCGTATAGCATAC | 41 |
| KanMX f1 | GACTCACGTTTCGAGGCCGCG | 42 |
| KanMX r1 | TGGTATCGGTCTGCGATTCCGA | 43 |
| cyc term with hph overlap | CGCTCGAAGGCTTTAATTTGCGGCCGGTACGAAGCTTCAGAGCTTGCCTTGTCCCCGCCGG | 44 |
| gal1p from pct271 | AGTACGGATTAGAAGCCGCCGAGCGGG | 45 |
| cyc term rev F | CTGAAGCTTCGTACCGGCCGC | 46 |
| o-GIL 104-extR1 | TGAGAAGTTGTTCTGAACAAAGTAAAAAAAAGAAGTATACTAATACGACTCACTATAGGG | 47 |

TABLE 3 -continued

Primers used in this study.

| Primer ID | Primer Sequence | SEQ ID NO: |
|---|---|---|
| cyc term F-ura3 prom F | TGGGACGCTCGAAGGCTTTAATTTGCGGCCGGTACG AAGCTTCGATTCGGTAATCTCCGAACAG | 48 |
| gal1 end R-ura3 term R | TGAGAAGTTGTTCTGAACAAAGTAAAAAAAGAAG TATACTTAAGGGTAATAACTGATATAATTAAATTG | 49 |
| ACT1-GEV_to_CAN1 FOR | GCACAAATTAGCAGAAAGAAGAGTGGTTGCGAACA GAGTAAACCGAATCAGGGAATCCCGGCGCGCCGCC TCTACCTTGCAGACC | 50 |
| ACT1-GEV_to_CAN1 REV | CGGTGTATGACTTATGAGGGTGAGAATGCGAAATG GCGTGGAAATGTGATCAAAGGGGATCCTACCCACC GTACTCGTCAATTCC | 51 |

REFERENCES

BOYLE, E. I., S. A. WENG, J. GOLLUB, H. JIN, D. BOTSTEIN et al., 2004 GO::TermFinder-open source software for accessing Gene Ontology information and finding significantly enriched Gene Ontology terms associated with a list of genes. Bioinformatics 20: 3710-3715.

BRAUER, M. J., C. HUTTENHOWER, E. M. AIROLDI, R. ROSENSTEIN, J. C. MATESE et al., 2008 Coordination of growth rate, cell cycle, stress response, and metabolic activity in yeast. Molecular Biology of the Cell 19: 352-367.

CAI, L., C. K. DALAL and M. B. ELOWITZ, 2008 Frequency-modulated nuclear localization bursts coordinate gene regulation. Nature 455: 485-U416.

DEVIRGILIO, C., N. BURCKERT, W. BELL, P. JENO, T. BOLLER et al., 1993 Disruption of Tps2, the Gene Encoding the 100-Kda Subunit of the Trehalose-6-Phosphate Synthase Phosphatase Complex in Saccharomyces-Cerevisiae, Causes Accumulation of Trehalose-6-Phosphate and Loss of Trehalose-6-Phosphate Phosphatase-Activity. European Journal of Biochemistry 212: 315-323.

GAO, C. Y., and J. L. PINKHAM, 2000 Tightly regulated, beta-estradiol dose-dependent expression system for yeast. Biotechniques 29: 1226-1231.

GAISNE, M., BECAM, A. M., VERDIERE, J., AND HERBERT, C. J. (1999). A 'natural' mutation in Saccharomyces cerevisiae strains derived from S288c affects the complex regulatory gene HAP1 (CYP1). Curr Genet. 36, 195-200.

GILL, G., and M. PTASHNE, 1988 Negative Effect of the Transcriptional Activator Gal4. Nature 334: 721-724.

GINIGER, E., S. M. VARNUM and M. PTASHNE, 1985 Specific DNA-Binding of Gal4, a Positive Regulatory Protein of Yeast. Cell 40: 767-774.

GOLDSTEIN, A. L., and J. H. MCCUSKER, 1999 Three new dominant drug resistance cassettes for gene disruption in Saccharomyces cerevisiae. Yeast 15: 1541-1553.

GUARENTE, L., AND PTASHNE, M. (1981). Fusion of Escherichia-Coli-Lacz to the Cytochrome-C Gene of Saccharomyces-Cerevisiae. P Natl Acad Sci-Biol 78, 2199-2203.

GUELDENER, U., J. HEINISCH, G. J. KOEHLER, D. Voss and J. H. HEGEMANN, 2002 A second set of loxP marker cassettes for Cre-mediated multiple gene knockouts in budding yeast. Nucleic Acids Res 30: e23.

GULDENER, U., S. HECK, T. FIELDER, J. BEINHAUER and J. H. HEGEMANN, 1996 A new efficient gene disruption cassette for repeated use in budding yeast. Nucleic Acids Res 24: 2519-2524.

HERSEN, P., MCCLEAN, M. N., MAHADEVAN, L., AND RAMANATHAN, S. (2008). Signal Processing by the HOG MAP kinase pathway. P Natl Acad Sci USA 105, 7165-7170.

HICKMAN, M. J. AND WINSTON, F (2007). Heme Levels Switch the Function of Hap1 of Saccharomyces cerevisiae between Transcriptional Activator and Transcriptional Repressor. Molecular and Cellular Biology, 27, 7414-7424.

HICKMAN, M. J., PETTI, A. A., HO-SHING, O., SILVERMAN, S. J., MCISAAC, R. S., LEE, T. A., AND BOTSTEIN, D. (2011). Complex co-regulation of sulfur and phospholipid metabolism reflects the importance of methylation in the growth of yeast. In preparation.

HONG, M. Q., M. X. FITZGERALD, S. HARPER, C. LUO, D. W. SPEICHER et al., 2008 Structural basis for dimerization in DNA recognition by Gal4. Structure 16: 1019-1026.

HOVLAND, P., J. FLICK, M. JOHNSTON and R. A. SCLAFANI, 1989 Galactose as a Gratuitous Induced of Gal Gene-Expression in Yeasts Growing on Glucose. Gene 83: 57-64.

KAHM, M., G. HASENBRINK, H. LICHTENBERG-FRATE, J. LUDWIG and M. KSCHISCHO, 2010 grofit: Fitting Biological Growth Curves with R. Journal of Statistical Software 33: 1-21.

LABOW, M. A., S. B. BAIM, T. SHENK and A. J. LEVINE, 1990 Conversion of the Lac Repressor into an Allosterically Regulated Transcriptional Activator for Mammalian-Cells. Molecular and Cellular Biology 10: 3343-3356.

LIKO, D., SLATTERY, M. G., PHILLIPS, C. L., AND HEIDEMAN, W. (2006). Using the yeast gene deletion collection to customize gene expression. Biotechniques 40, 728-+.

LIU, X. D., MORANO, K. A., AND THIELE, D. J. (1999). The yeast Hsp110 family member, SSE1, is an Hsp90 cochaperone. J Biol Chem 274, 26654-26660.

LONGTINE, M. S., A. MCKENZIE, 3RD, D. J. DEMARINI, N. G. SHAH, A. WACH et al., 1998 Additional modules for versatile and economical PCR-based gene deletion and modification in Saccharomyces cerevisiae. Yeast 14: 953-961.

LOUVION, J. F., B. HAVAUXCOPF and D. PICARD, 1993 Fusion of Gal4-Vp16 to a Steroid-Binding Domain Provides a Tool for Gratuitous Induction of Galactose-Responsive Genes in Yeast. Gene 131: 129-134.

LU, C., M. J. BRAUER and D. BOTSTEIN, 2009 Slow Growth Induces Heat-Shock Resistance in Normal and Respiratory-deficient Yeast. Molecular Biology of the Cell 20: 891-903.

MA, H., S. KUNES, P. J. SCHATZ and D. BOTSTEIN, 1987 Plasmid construction by homologous recombination in yeast. Gene 58: 201-216.

MARMORSTEIN, R., M. CAREY, M. PTASHNE and S. C. HARRISON, 1992 DNA Recognition by Gal4—Structure of a Protein DNA Complex. Nature 356: 408-414.

MASON, P. B., and K. STRUHL, 2005 Distinction and relationship between elongation rate and processivity of RNA polymerase II in vivo. Mol Cell 17: 831-840.

MASSELOT, M., AND ROBICHON-SZULMAJSTER, H. (1975). Methionine Biosynthesis in Saccharomyces cerevisiae. Molecular and General Genetics 139, 121-132.

MCCLEAN, M. N., HERSEN, P., AND RAMANATHAN, S. (2011). Measuring In Vivo Signaling Kinetics in a Mitogen-Activated Kinase Pathway Using Dynamic Input Stimulation. Methods Mol Biol 734.

PRATT, W. B., and D. O. TOFT, 1997 Steroid receptor interactions with heat shock protein and immunophilin chaperones. Endocrine Reviews 18: 306-360.

QUINTERO, M. J., D. MAYA, M. AREVALO-RODRIGUEZ, A. CEBOLLA and S. CHAVEZ, 2007 An improved system for estradiol-dependent regulation of gene expression in yeast. Microbial Cell Factories 6: —.

RONEN, M., and D. BOTSTEIN, 2006 Transcriptional response of steady-state yeast cultures to transient perturbations in carbon source. Proceedings of the National Academy of Sciences of the United States of America 103: 389-394.

ROUILLON, A., BARBEY, R., PATTON, E. E., TYERS, M., AND THOMAS, D. (2000). Feedback-regulated degradation of the transcriptional activator Met4 is triggered by the SCFMet30 complex. Embo J 19, 282-294.

SADOWSKI, I., J. MA, S. TRIEZENBERG and M. PTASHNE, 1988 Gal4-Vp16 Is an Unusually Potent Transcriptional Activator. Nature 335: 563-564.

SHEFF, M. A., AND THORN, K. S. (2004). Optimized cassettes for fluorescent protein tagging in Saccharomyces cerevisiae. Yeast 21, 661-670.

SIKORSKI AND HEITER, (1989). A system of shuttle vectors and yeast host strains designed for efficient manipulation of DNA in Saccharomyces cerevisiae. Genetics 122, 19-27.

SILVERMAN, S. J., PETTI, A. A., SLAVOV, N., PARSONS, L., BRIEHOF, R., THIBERGE, S. Y., ZENKLUSEN, D., GANDHI, S. J., LARSON, D. R., SINGER, R. H., AND BOTSTEIN, D. (2010). Metabolic cycling in single yeast cells from unsynchronized steady-state populations limited on glucose or phosphate. P Natl Acad Sci USA 107, 6946-6951.

STERNBERG, S. R., 1983 Biomedical Image-Processing. Computer 16: 22-34.

TAKAHASHI, S., AND PRYCIAK, P. M. (2008). Membrane localization of scaffold proteins promotes graded signaling in the yeast MAP kinase cascade. Curr Biol 18, 1184-1191.

TAXIS, C., G. STIER, R. SPADACCINI and M. KNOP, 2009 Efficient protein depletion by genetically controlled deprotection of a dormant N-degron. Mol Syst Biol 5: 267.

VEATCH, J. R., M. A. MCMURRAY, Z. W. NELSON and D. E. GOTTSCHLING, 2009 Mitochondrial Dysfunction Leads to Nuclear Genome Instability via an Iron-Sulfur Cluster Defect. Cell 137: 1247-1258.

ZENKLUSEN, D., D. R. LARSON and R. H. SINGER, 2008 Single-RNA counting reveals alternative modes of gene expression in yeast. Nature Structural & Molecular Biology 15: 1263-1271.

---

The invention claimed is:

1. A method of targeted graded protein depletion in a eukaryotic cell comprising:
  a. providing a eukaryotic cell comprising:
    i. a target gene having a modified degron sequence at the initiator codon of the open reading frame, the target gene being capable of expressing a target protein;
    ii. a protease-encoding gene that expresses a protease that is capable of hydrolyzing the target protein to yield a protein having an N-end rule destabilizing amino acid at the amino terminus;
    iii. a transcriptional activator comprising a DNA-binding domain and a hormone-binding domain, wherein, when bound by a hormone, the transcriptional activator induces expression of the protease-encoding gene; and
    vi. a transcriptional activator gene comprising a constitutive promoter that expresses the transcriptional activator at a level that is sufficient to achieve a graded response of activation to hormone induction; and
  b. exposing the eukaryotic cell to an amount of a hormone that is effective to induce the transcriptional activator in a graded response to the hormone; wherein the hormone binds to the hormone-binding domain of the transcriptional activator, the hormone-bound transcriptional activator induces expression of the protease by the protease-encoding gene, the protease cleaves the target protein to expose the N-end rule destabilizing amino acid and the target protein is degraded.

2. The method of claim 1 wherein the DNA-binding domain is a GAL4 DNA binding domain, a zinc finger domain, or a DNA-binding domain of a transcriptional activator that is not from yeast.

3. The method of claim 1 wherein the hormone-binding domain is from the human estradiol receptor, the human glucocorticoid receptor or the human mineralocorticoid receptor.

4. The method of claim 1 wherein the transcriptional activator is GEV, the hormone is β-estradiol, and the protease-encoding gene encodes the tobacco etch virus (TEV) protease.

5. The method of claim 1 wherein the protease-encoding gene is driven by a synthetic promoter operably linked to a modified TEV protease-coding region, a spliceosome subunit p14-peptide coding region, a terminator, and a selectable marker.

6. The method of claim 1 wherein the protease is TEV, HRV 2A or HRV 3C.

7. A eukaryotic cell comprising:
  a. a target gene having a modified degron sequence at the initiator codon of the open reading frame, the target gene being capable of expressing a target protein;
  b. a protease-encoding gene that expresses a protease that is capable of hydrolyzing the target protein to yield a cleaved target protein having an N-end rule destabilizing amino acid at the amino terminus;
  c. transcriptional activator comprising a hormone-binding domain, wherein, when bound by a hormone, the transcriptional activator induces transcription of the protease-encoding gene;
  d. a transcriptional activator gene comprising a constitutive promoter that expresses the transcriptional activator at a level that is sufficient to achieve a graded response of activation to hormone induction.

8. The cell of claim 7 wherein the transcriptional activator is GEV, ZEV or 4ZEV, and the hormone is β-estradiol.

* * * * *

SEQUENCE LISTING

```
<160> NUMBER OF SEQ ID NOS: 53

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(14)
<223> OTHER INFORMATION: a, c, t, g, unknown or other

<400> SEQUENCE: 1
cggnnnnnnn nnnnccg                                                  17

<210> SEQ ID NO 2
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2 gcgtgggcg                                                            9

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 3
gcggcggagg ag                                                          12

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gcgsskgmgv mk                                                          12

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Ile Ser Thr Leu
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Asn Ser Ser Met
1               5

<210> SEQ ID NO 7
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Thr Arg Pro Tyr Ala Cys Pro Val Glu Ser Cys Asp Arg Arg Phe
1               5                   10                  15

Ser Arg Ser Asp Glu Leu Thr Arg His Ile Arg Ile His Thr Gly Gln
            20                  25                  30

Lys Pro Phe Gln Cys Arg Ile Cys Met Arg Asn Phe Ser Arg Ser Asp
        35                  40                  45

His Leu Thr Thr His Ile Arg Thr His Thr Gly Glu Lys Pro Phe Ala
    50                  55                  60

Cys Asp Ile Cys Gly Arg Lys Phe Ala Arg Ser Asp Glu Arg Lys Arg
65                  70                  75                  80

His Thr Lys Ile His Thr Gly
                85

<210> SEQ ID NO 8
<211> LENGTH: 116
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 8

Gly Thr Arg Pro Tyr Ala Cys Pro Val Glu Ser Cys Asp Arg Arg Phe
1               5                   10                  15

Ser Arg His Ala Asn Leu Thr Arg His Ile Arg Ile His Thr Gly Gln
            20                  25                  30

Lys Pro Phe Gln Cys Arg Ile Cys Met Arg Asn Phe Ser Arg Asn Ala
        35                  40                  45

Asn Leu Val Arg His Ile Arg Thr His Thr Gly Ser Gln Lys Pro Phe
    50                  55                  60

Gln Cys Arg Ile Cys Met Arg Asn Phe Ser Arg Lys Ala Asp Leu Arg
65                  70                  75                  80

Arg His Ile Arg Thr His Thr Gly Glu Lys Pro Phe Ala Cys Asp Ile
                85                  90                  95

Cys Gly Arg Lys Phe Ala Arg Lys Gly Asp Leu Lys Arg His Thr Lys
            100                 105                 110

Ile His Thr Gly
        115

<210> SEQ ID NO 9
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9 gcgtgggtg                                                                  9

<210> SEQ ID NO 10
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10 gcgtgggag                                                                  9

<210> SEQ ID NO 11
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11 gcgtgggcc                                                                  9

<210> SEQ ID NO 12
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
```

-continued gcgtggggg                                                             9

<210> SEQ ID NO 13
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gcgtgggcgt gcgtgggcgg gcgtgggcgt gcgtgggcgg gcgtgggcgt gcgtgggcg      59

<210> SEQ ID NO 14
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gcggcggagg agtgcggcgg aggaggagcg gcggaggagt gcggcggagg aggagcggcg      60
gaggagtgcg gcggaggag                                                  79

<210> SEQ ID NO 15
<211> LENGTH: 54
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(1)
<223> OTHER INFORMATION: Amino-allyl-Cy3 labeled thymidine
<220> FEATURE:
<221> NAME/KEY: misc_feature
<222> LOCATION: (14)..(14)
<223> OTHER INFORMATION: Amino-allyl-Cy3 labeled thymidine
<220> FEATURE:
<221> NAME/KEY: misc_feature
<222> LOCATION: (28)..(28)
<223> OTHER INFORMATION: Amino-allyl-Cy3 labeled thymidine
<220> FEATURE:
<221> NAME/KEY: misc_feature
<222> LOCATION: (40)..(40)
<223> OTHER INFORMATION: Amino-allyl-Cy3 labeled thymidine
<220> FEATURE:
<221> NAME/KEY: misc_feature
<222> LOCATION: (53)..(53)
<223> OTHER INFORMATION: Amino-allyl-Cy3 labeled thymidine

<400> SEQUENCE: 15
tctctttgct ttttcctggc ctcgctgtag ttctgctcct cgttatagcc tctt           54

<210> SEQ ID NO 16
<211> LENGTH: 54
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(1)
<223> OTHER INFORMATION: Amino-allyl-Cy3 labeled thymidine
<220> FEATURE:
<221> NAME/KEY: misc_feature
<222> LOCATION: (13)..(13)

<223> OTHER INFORMATION: Amino-allyl-Cy3 labeled thymidine
<220> FEATURE:
<221> NAME/KEY: misc_feature
<222> LOCATION: (25)..(25)
<223> OTHER INFORMATION: Amino-allyl-Cy3 labeled thymidine
<220> FEATURE:
<221> NAME/KEY: misc_feature
<222> LOCATION: (38)..(38)
<223> OTHER INFORMATION: Amino-allyl-Cy3 labeled thymidine
<220> FEATURE:
<221> NAME/KEY: misc_feature
<222> LOCATION: (52)..(52)
<223> OTHER INFORMATION: Amino-allyl-Cy3 labeled thymidine

<400> SEQUENCE: 16
ttcgcgttcg tttgattaga tgtgtgggca tcagaactat cttcctggcc ctgg        54

<210> SEQ ID NO 17
<211> LENGTH: 54
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(1)
<223> OTHER INFORMATION: Amino-allyl-Cy3 labeled thymidine
<220> FEATURE:
<221> NAME/KEY: misc_feature
<222> LOCATION: (14)..(14)
<223> OTHER INFORMATION: Amino-allyl-Cy3 labeled thymidine
<220> FEATURE:
<221> NAME/KEY: misc_feature
<222> LOCATION: (28)..(28)
<223> OTHER INFORMATION: Amino-allyl-Cy3 labeled thymidine
<220> FEATURE:
<221> NAME/KEY: misc_feature
<222> LOCATION: (41)..(41)
<223> OTHER INFORMATION: Amino-allyl-Cy3 labeled thymidine
<220> FEATURE:
<221> NAME/KEY: misc_feature
<222> LOCATION: (53)..(53)
<223> OTHER INFORMATION: Amino-allyl-Cy3 labeled thymidine

<400> SEQUENCE: 17
ttctggccca cgatcgtgtt ctgccaatgg tatgagcatg tcgtttttag attg        54

<210> SEQ ID NO 18
<211> LENGTH: 54
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(1)
<223> OTHER INFORMATION: Amino-allyl-Cy3 labeled thymidine
<220> FEATURE:
<221> NAME/KEY: misc_feature
<222> LOCATION: (14)..(14)
<223> OTHER INFORMATION: Amino-allyl-Cy3 labeled thymidine
<220> FEATURE:
<221> NAME/KEY: misc_feature
<222> LOCATION: (28)..(28)
<223> OTHER INFORMATION: Amino-allyl-Cy3 labeled thymidine
<220> FEATURE:
<221> NAME/KEY: misc_feature
<222> LOCATION: (41)..(41)
<223> OTHER INFORMATION: Amino-allyl-Cy3 labeled thymidine
<220> FEATURE:
<221> NAME/KEY: misc_feature
<222> LOCATION: (53)..(53)
<223> OTHER INFORMATION: Amino-allyl-Cy3 labeled thymidine

<400> SEQUENCE: 18
ttacttgatt ctctcacggg caggaggtcg cttaaaacgt tgattgcagt gttg        54

<210> SEQ ID NO 19
<211> LENGTH: 54
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(1)
<223> OTHER INFORMATION: Amino-allyl-Cy3 labeled thymidine
<220> FEATURE:
<221> NAME/KEY: misc_feature
<222> LOCATION: (14)..(14)
<223> OTHER INFORMATION: Amino-allyl-Cy3 labeled thymidine
<220> FEATURE:
<221> NAME/KEY: misc_feature
<222> LOCATION: (26)..(26)
<223> OTHER INFORMATION: Amino-allyl-Cy3 labeled thymidine
<220> FEATURE:
<221> NAME/KEY: misc_feature
<222> LOCATION: (40)..(40)
<223> OTHER INFORMATION: Amino-allyl-Cy3 labeled thymidine
<220> FEATURE:
<221> NAME/KEY: misc_feature
<222> LOCATION: (53)..(53)
<223> OTHER INFORMATION: Amino-allyl-Cy3 labeled thymidine

<400> SEQUENCE: 19
tcccagttct tcctgcagtt tctcatttgc actggctaat tgcgatgcgt tttg        54

<210> SEQ ID NO 20
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gatgtttacc gatgcccttg gaattgacga gtacggtggg ggtgacggtg ctggttta     58

<210> SEQ ID NO 21
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttgacctcta atcatgcggc cgctctagaa ctagtggatc tcgatgaatt cgagctcg     58

<210> SEQ ID NO 22
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tactagggct gttaccaaat actcctcctc tactcaagcc ggtgacggtg ctggttta     58

<210> SEQ ID NO 23

-continued

```
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aaaagaaaac atgactaaat cacaatacct agtgagtgac tcgatgaatt cgagctcg      58

<210> SEQ ID NO 24
<211> LENGTH: 67
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgctgtatga gtcgccttcg tgggactgct cctgcttcat tatagttttt tctccttgac    60
gttaaag                                                              67

<210> SEQ ID NO 25
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tctcgtcaat aaagcgcact tctgataagc acttttattc gcaattaaga actaaaagat    60
atagagtgc                                                            69

<210> SEQ ID NO 26
<211> LENGTH: 67
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cctcagtaga aagcttatta ttatttgcca gagagttcat tatagttttt tctccttgac    60
gttaaag                                                              67

<210> SEQ ID NO 27
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
agtgcttaaa atataatacg gttttctaca cttttattaa gcaattaaga actaaaagat    60
atagagtgc                                                            69

<210> SEQ ID NO 28
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 28
aaaccaaaat aacactgcct gtcactattt ctgtgccgaa gcaattaaga actaaaagat        60

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29 tctcttctttt ggagaattgt cttgggcagt ggtggtcatt atagtttttt ctccttgacg       60

<210> SEQ ID NO 30
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aaagcgcact tctgataagc acttttattc cttttttttcc actgtgaacg atgtctatta      60
cttctttgta caag                                                         74

<210> SEQ ID NO 31
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccgtgctgta tgagtcgcct tcgtgggact gctcctgctt cattaataac ttcgtatagc      60
atac                                                                    64

<210> SEQ ID NO 32
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aaaaagctga agcttaaag aagcaaattt ttgagaaggt tcagaaagaa cggatccccg        60
ggttaattaa                                                              70

<210> SEQ ID NO 33
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atgcacgtat atatatatat atatataatt aaactgtata gtctgttatt gaattcgagc       60
tcgtttaaac                                                              70

<210> SEQ ID NO 34
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gttgggctca atatacacag tcgatagtct atatgtgcat atgtctatta cttctttgta    60
caag                                                                64

<210> SEQ ID NO 35
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gagaaatatt tcatctacat tcatgtcttg cgccagtttc attaataact tcgtatagca    60
tac                                                                 63

<210> SEQ ID NO 36
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
taacaatttc acacaggaaa cagctatgac catgattacg tctattactt ctttgtac      58

<210> SEQ ID NO 37
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cagggttttc ccagtcacga cgttgtaaaa cgacggccag catcgatgaa ttctctgtcg    60
tcc                                                                 63

<210> SEQ ID NO 38
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gctggttatg ttcctattcg aactccagct catatggata taacttcgta taatgtatgc    60

<210> SEQ ID NO 39
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cggccgcata ggccactagt ggatctgata tcatcgataa taacttcgta tagcatac    58

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
atgtctatta cttctttgta caag    24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cattaataac ttcgtatagc atac    24

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gactcacgtt tcgaggccgc g    21

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tggtatcggt ctgcgattcc ga    22

<210> SEQ ID NO 44
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cgctcgaagg ctttaatttg cggccggtac gaagcttcag agcttgcctt gtccccgccg    60
g    61

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 45
agtacggatt agaagccgcc gagcggg                                        27

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ctgaagcttc gtaccggccg c                                              21

<210> SEQ ID NO 47
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tgagaagttg ttctgaacaa agtaaaaaaa agaagtatac taatacgact cactataggg    60

<210> SEQ ID NO 48
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tgggacgctc gaaggcttta atttgcggcc ggtacgaagc ttcgattcgg taatctccga    60
acag                                                                 64

<210> SEQ ID NO 49
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tgagaagttg ttctgaacaa agtaaaaaaa agaagtatac ttaagggtaa taactgatat    60
aattaaattg                                                           70

<210> SEQ ID NO 50
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gcacaaatta gcagaaagaa gagtggttgc gaacagagta aaccgaatca gggaatcccg    60
gcgcgccgcc tctaccttgc agacc                                          85

<210> SEQ ID NO 51
<211> LENGTH: 85
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cggtgtatga cttatgaggg tgagaatgcg aaatggcgtg gaaatgtgat caaaggggat    60
cctacccacc gtactcgtca attcc                                          85

<210> SEQ ID NO 52
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(321)

<400> SEQUENCE: 52 atg tct att act tct ttg tac aag aag gct ggt tct gaa aac ttg tac     48
Met Ser Ile Thr Ser Leu Tyr Lys Lys Ala Gly Ser Glu Asn Leu Tyr
1               5                   10                  15 ttc caa ttc cac aag tct ggt gct tgg aag ttg cca gtt tct ttg gtt     96
Phe Gln Phe His Lys Ser Gly Ala Trp Lys Leu Pro Val Ser Leu Val
            20                  25                  30 aag aga ggg atc gat aag ctt gat tat aaa gaa cag ctt cag gct tgg    144
Lys Arg Gly Ile Asp Lys Leu Asp Tyr Lys Glu Gln Leu Gln Ala Trp
        35                  40                  45 cgg tgg gaa aga gaa att gat gag aga aat cgc cca ctt tct gat gag    192
Arg Trp Glu Arg Glu Ile Asp Glu Arg Asn Arg Pro Leu Ser Asp Glu
    50                  55                  60 gaa tta gat gct atg ttc cca gaa gga tat aag gta ctt cct cct cca    240
Glu Leu Asp Ala Met Phe Pro Glu Gly Tyr Lys Val Leu Pro Pro Pro
65                  70                  75                  80 gct ggt tat gtt cct att cga act cca gct cat atg gat ata act tcg    288
Ala Gly Tyr Val Pro Ile Arg Thr Pro Ala His Met Asp Ile Thr Ser
                85                  90                  95 tat aat gta tgc tat acg aag tta tta tcg atg                        321
Tyr Asn Val Cys Tyr Thr Lys Leu Leu Ser Met
            100                 105

<210> SEQ ID NO 53
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Ser Ile Thr Ser Leu Tyr Lys Lys Ala Gly Ser Glu Asn Leu Tyr
1               5                   10                  15

Phe Gln Phe His Lys Ser Gly Ala Trp Lys Leu Pro Val Ser Leu Val
            20                  25                  30

Lys Arg Gly Ile Asp Lys Leu Asp Tyr Lys Glu Gln Leu Gln Ala Trp
        35                  40                  45

Arg Trp Glu Arg Glu Ile Asp Glu Arg Asn Arg Pro Leu Ser Asp Glu
    50                  55                  60

Glu Leu Asp Ala Met Phe Pro Glu Gly Tyr Lys Val Leu Pro Pro Pro
65                  70                  75                  80

```
Ala Gly Tyr Val Pro Ile Arg Thr Pro Ala His Met Asp Ile Thr Ser
                85                  90                  95

Tyr Asn Val Cys Tyr Thr Lys Leu Leu Ser Met
            100             105
```